(12) United States Patent
Agrafiotis et al.

(10) Patent No.: US 6,295,514 B1
(45) Date of Patent: *Sep. 25, 2001

(54) METHOD, SYSTEM, AND COMPUTER PROGRAM PRODUCT FOR REPRESENTING SIMILARITY/DISSIMILARITY BETWEEN CHEMICAL COMPOUNDS

(75) Inventors: Dimitris K. Agrafiotis, Downington; Victor S. Lobanov; Francis R. Salemme, both of Yardley, all of PA (US)

(73) Assignee: 3-Dimensional Pharmaceuticals, Inc., Exton, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/963,872

(22) Filed: Nov. 4, 1997

Related U.S. Application Data

(60) Provisional application No. 60/030,187, filed on Nov. 4, 1996.

(51) Int. Cl.⁷ .............................. G06G 7/58; G06G 7/48
(52) U.S. Cl. .......................... 703/12; 703/2; 702/27; 702/28; 702/30; 702/31; 702/32; 702/179; 702/180; 702/181
(58) Field of Search .................. 395/500.33; 702/27, 702/28, 30, 31, 32, 179, 180, 181; 703/12

(56) References Cited

U.S. PATENT DOCUMENTS

| | | | |
|---|---|---|---|
| 4,773,099 | 9/1988 | Bokser | 382/14 |
| 4,811,217 | 3/1989 | Tokizane et al. | 364/300 |
| 4,859,736 | 8/1989 | Rink | 525/54.1 |
| 4,908,773 | 3/1990 | Pantoliano et al. | 364/496 |
| 4,935,875 | 6/1990 | Shah et al. | 364/497 |

(List continued on next page.)

FOREIGN PATENT DOCUMENTS

| | | | | |
|---|---|---|---|---|
| 0 355 266 B1 | 6/1993 | (EP) | | B01J/19/00 |
| 0 355 628 B1 | 11/1993 | (EP) | | G21F/9/00 |

(List continued on next page.)

OTHER PUBLICATIONS

Gasteiger et al, "Assessment of the Diversity of Combinatorial Libraries by an Encoding of Molecular Surface Properties", Abstracts of Papers, American Chemical Society, 211th ACS National Meeting, Item 070, Mar. 1996.*
Appl. No. 09/303,671 Agrafiotis et al. May 3, 1999.
Appl. No. 08/963,870 Agrafiotis et al. Nov. 4, 1997.
Appl. No. 09/073,845 Agrafiotis et al. May, 7, 1998.

(List continued on next page.)

Primary Examiner—Kevin J. Teska
Assistant Examiner—Samuel Broda
(74) Attorney, Agent, or Firm—Sterne, Kessler, Goldstein & Fox PLLC

(57) ABSTRACT

A system method, and computer program product for visualizing and interactively analyzing data relating to chemical compounds. A user selects a plurality of compounds to map, and also selects a method for evaluating similarity/dissimilarity between the selected compounds. A non-linear map is generated in accordance with the selected compounds and the selected method. The non-linear map has a point for each of the selected compounds, wherein a distance between any two points is representative of similarity/dissimilarity between the corresponding compounds. A portion of the non-linear map is then displayed. Users are enabled to interactively analyze compounds represented in the non-linear map.

42 Claims, 13 Drawing Sheets

U.S. PATENT DOCUMENTS

| | | | |
|---|---|---|---|
| 4,939,666 | 7/1990 | Hardman | 436/89 |
| 5,010,175 | 4/1991 | Rutter et al. | 530/334 |
| 5,025,388 | 6/1991 | Cramer, III et al. | 364/496 |
| 5,155,801 | 10/1992 | Lincoln | 395/22 |
| 5,167,009 | 11/1992 | Skeirik | 395/27 |
| 5,181,259 | 1/1993 | Rorvig | 382/36 |
| 5,240,680 | 8/1993 | Zuckerman et al. | 422/67 |
| 5,260,882 | 11/1993 | Blanco et al. | 364/499 |
| 5,265,030 | 11/1993 | Skolnick et al. | 364/496 |
| 5,270,170 | 12/1993 | Schatz et al. | 435/7.37 |
| 5,288,514 | 2/1994 | Ellman | 427/2 |
| 5,307,287 | 4/1994 | Cramer, III et al. | 364/496 |
| 5,323,471 | 6/1994 | Hayashi | 382/15 |
| 5,331,573 | 7/1994 | Balaji et al. | 364/500 |
| 5,434,796 | 7/1995 | Weininger | 364/496 |
| 5,436,850 | 7/1995 | Eisenberg et al. | 364/496 |
| 5,442,122 | 8/1995 | Noda et al. | 564/426 |
| 5,463,564 | 10/1995 | Agrafiotis et al. | 364/496 |
| 5,499,193 | 3/1996 | Sugawara et al. | 364/500 |
| 5,519,635 | 5/1996 | Miyake et al. | 364/497 |
| 5,524,065 | 6/1996 | Yagasaki | 382/226 |
| 5,526,281 | 6/1996 | Chapman et al. | 364/496 |
| 5,545,568 | 8/1996 | Ellman | 436/518 |
| 5,549,974 | 8/1996 | Holmes | 428/403 |
| 5,553,225 | 9/1996 | Perry | 395/157 |
| 5,565,325 | 10/1996 | Blake | 435/7.1 |
| 5,574,656 | 11/1996 | Agrafiotis et al. | 364/500 |
| 5,585,277 | 12/1996 | Bowie et al. | 436/518 |
| 5,602,755 | 2/1997 | Ashe et al. | 364/498 |
| 5,602,938 | 2/1997 | Akiyama et al. | 382/155 |
| 5,612,895 | 3/1997 | Balaji et al. | 364/496 |
| 5,634,017 | 5/1997 | Mohanty et al. | 395/326 |
| 5,635,598 | 6/1997 | Lebl et al. | 530/334 |
| 5,670,326 | 9/1997 | Beutel | 435/7.1 |
| 5,679,582 | 10/1997 | Bowie et al. | 436/518 |
| 5,684,711 | 11/1997 | Agrafiotis et al. | 364/500 |
| 5,703,792 | 12/1997 | Chapman | 364/496 |
| 5,712,171 | 1/1998 | Zambias et al. | 436/518 |
| 5,712,564 | 1/1998 | Hayosh | 324/210 |
| 5,736,412 | 4/1998 | Zambias et al. | 436/518 |
| 5,740,326 | 4/1998 | Boulet et al. | 395/27 |
| 5,789,160 | 8/1998 | Eaton et al. | 435/6 |
| 5,807,754 | 9/1998 | Zambias et al. | 436/518 |
| 5,811,241 | 9/1998 | Goodfellow et al. | 435/7.1 |
| 5,832,494 | * 11/1998 | Egger et al. | 707/102 |
| 5,858,650 | 1/1999 | Eaton et al. | 435/6 |
| 5,861,532 | 1/1999 | Brown et al. | 564/142 |
| 5,866,334 | 2/1999 | Beutel | 435/6 |
| 5,901,069 | 5/1999 | Agrafiotis et al. | 364/528.03 |
| 5,908,960 | 6/1999 | Newlander | 564/177 |
| 5,933,819 | 8/1999 | Skolnick et al. | 706/21 |
| 6,014,661 | 1/2000 | Ahlberg et al. | 707/3 |
| 6,037,135 | 3/2000 | Kubo et al. | 435/7.24 |
| 6,049,797 | 4/2000 | Guha et al. | 707/6 |

FOREIGN PATENT DOCUMENTS

| | | | |
|---|---|---|---|
| 0 770 876 A1 | 5/1997 | (EP) | G01N/33/68 |
| 0 818 744 A2 | 1/1998 | (EP) | G06F/17/50 |
| WO 91/19735 | 12/1991 | (WO) | C07K/7/02 |
| WO 92/00091 | 1/1992 | (WO) | A61K/37/02 |
| WO 93/20242 | 10/1993 | (WO) | C12Q/1/70 |
| WO 94/28504 | 12/1994 | (WO) | G06F/15/60 |
| WO 95/01606 | 1/1995 | (WO) | G06F/15/42 |
| WO 97/09342 | 3/1997 | (WO) | C07H/21/02 |
| WO 97/20952 | 6/1997 | (WO) | C12Q/1/68 |
| WO 97/27559 | 7/1997 | (WO) | G06F/19/00 |
| WO 98/20459 | 5/1998 | (WO) | G06T/11/20 |

OTHER PUBLICATIONS

Borg, Inger and Groenen, Patrick, *Modern Multidimensional Scaling Theory and Applications,* Springer Series in Statistics, 1997, entire book submitted.

Agrafiotis, D.K. et al., "Advances in diversity profiling and combinatorial series design," *Molecular Diversity,* vol. 4, 1999, pp. 1–22.

Agrafiotis, D.K. and Lobanov, V.S., "An Efficient Implementation of Distance–Based Diveristy Measure based on k–d Trees," *J. Chem. Inf. Comput. Sci.,* vol. 39, No. 1, Jan./Feb. 1999, pp. 51–58.

Agrafiotis, D.K. and Lobanov, V.S., "Bridging The Gap Between Diversity and QSAR," *Abstracts of Papers Part 1: 215th ACS National Meeting,* Mar. 29–Apr. 2, 1998, p. 181–COMP.

Agrafiotis, D.K. and Jaeger, E.P., "Directed Diversity®: An Operating System For Combinatorial Chemistry," *Abstracts of Papers Part 1: 211th ACS National Meeting,* Mar. 24–28, 1996, p. 46–COMP.

Agrafiotis, D.K., "Diversity of Chemical Libraries," *Encyclopedia of Computational Chemistry,* vol. 1:A–D, 1998, pp. 742–761.

Agrafiotis, D.K., "On the Use of Information Theory for Assessing Molecular Diversity," *J. Chem. Inf. Comput. Sci.,* vol. 37, No. 3, May/Jun. 1997, pp. 576–580.

Agrafiotis, D.K. et al., "Parallel QSAR," *Abstracts of Papers Part 1: 217th ACS National Meeting,* Mar. 21–25, 1999, p. 50–COMP.

Agrafiotis, D.K. et al., "PRODEN: A New Program for Calculating Integrated Projected Populations," *Journal of Computational Chemistry,* vol. 11, No. 9, Oct. 1990, pp. 1101–1110.

Agrafiotis, D.K. and Jaeger, E.P., "Stochastic Algorithms for Exploring Molecular Diversity," *Abstracts of Papers Part 1: 213th ACS National Meeting,* Apr. 13–17, 1997, p. 16–CINF.

Agrafiotis, D., "Theoretical Aspects of the Complex: Arts and New Technologies," *Applications and Impacts Information Processing '94,* vol. II, 1994, pp. 714–719.

Biswas, G. et al., "Evaluation of Projection Algorithms," *IEEE Transactions On Pattern Analysis And Machine Intellignece,* vol. PAMI–3, No. 6, Nov. 1981, pp. 701–708.

Bonchev, D. and Trinajstić, N., "Information theory, distance matrix, and molecular branching," *The Journal of Chemical Physics,* vol. 67, No. 10, Nov. 15, 1977, pp. 4517–4533.

Chang, C.L. and Lee, R.C.T., "A Heuristic Relaxation Method for Nonlinear Mapping in Cluster Analysis," *IEEE Transactions on Systems, Man, and Cybernetics,* vol. SMC–3, Mar. 1973, pp. 197–200.

Cramer, R.D. et al., "Virtual Compound Libraries: A New Approach to Decision Making in Molecular Discovery Research," *J. Chem. Inf. Comput. Sci.,* vol. 38, No. 6, Nov./Dec. 1998, pp. 1010–1023.

DeMers, D. and Cottrell, G., "Non–Linear Dimensionality Reduction," *Advances in Neural Information Processing Systems,* vol. 5, 1993, pp. 580–587.

Frey, P.W. and Slate, D.J., "Letter Recognition Using Holland–Style Adaptive Classifiers," *Machine Learning,* vol. 6, 1991, pp. 161–182.

Friedman, J.H., "Exploratory Projection Pursuit," *Journal of the American Statistical Association,* vol. 82, No. 397, Mar. 1987, pp. 249–266.

Friedman, J.H. and Tukey, J.W., "A Projection Pursuit Algorithm for Exploratory Data Analysis," *IEEE Transcations on Computers,* vol. C–23, No. 9, Sep. 1974, pp. 881–889.

Garrido, L. et al., "Use of Multilayer Feedforward Neural Nets As A Display Method for Multidimensional Distributions," *International Journal of Neural Systems,* vol. 6, No. 3, Sep. 1995, pp. 273–282.

Ghose, A.K. et al., "Prediction of Hydrophobic (Lipophilic) Properties of Small Organic Molecules Using Fragmental Methods: An Analysis of ALOGP and CLOGP Methods," *J. Phys. Chem. A,* vol. 102, No. 21, May 21, 1998, pp. 3762–3772.

Hall, L.H. and Kier, L.B., "The Molecular Connectivity Chi Indexes and Kappa Shape Indexes in Structure–Property Modeling," *Reviews in Computational Chemistry: Advances,* 1991, pp. 367–422.

Hecht–Nielsen, R., "Replicator Neural Networks for Universal Optimal Source Coding," *Science,* vol. 269, Sep. 29, 1995, pp. 1860–1863.

Hotelling, H., "Analysis of a Complex of Statistical Variables into Principal Components," *The Journal of Educational Psychology,* vol. XXIV, No. 6, Sep. 1933, pp. 417–441.

Hotelling, H., "Analysis of a Complex of Statistical Variables into Principal Components," *The Journal of Educational Psychology,* vol. XXIV, No. 7, Oct. 1933, pp. 498–520.

Lee, R.C.T. et al., "A Triangulation Method for the Sequential Mapping of Points from N–Space to Two–Space," *IEEE Transactions on Computers,* Mar. 1977, pp. 288–292.

Lipinski, C.A. et al., "Experimental and computational approaches to estimate solubility and permeability in drug discovery and development settings," *Advanced Drug Delivery Reviews,* vol. 23, 1997, pp. 3–25.

Lobanov, V.S. and Agrafiotis, D.K., "Intelligent Database Mining Techniques," *Abstracts of Papers Part 1: 215th ACS National Meeting,* Mar. 29–Apr. 2, 1998, p. 19–COMP.

Lobanov, V.S. et al., "Rational Selections from Virtual Libraries," *Abstracts of Papers Part 1: 217th ACS National Meeting,* Mar. 21–25, 1999, p. 181–COMP.

Mao, J. and Jain, A.K., "Artificial Neural Networks for Feature Extraction and Multivariate Data Projection," *IEEE transactions on Neural Networks,* vol. 6, No. 2, Mar. 1995, pp. 296–317.

Oja, E., "Principal Components, Minor Components, and Linear Neural Networks," *Neural Networks,* vol. 5, 1992, pp. 927–935.

Patterson, D.E. et al., "Neighborhood Behavior: A Useful Concept for Validation of 'Molecular Diversity' Descriptors," *Journal of Medicinal Chemistry,* vol. 39, No. 16, 1996, pp. 3049–3059.

Pykett, C.E., "Improving the Efficiency of Sammon's Nonlinear Mapping by Using Clustering Archetypes," *Electronics Letters,* vol. 14, No. 25, Dec. 7, 1978, pp. 799–800.

Rubner, J. and Tavan, P., "A Self–Organizing Network for Principal–Component Analysis," *Europhysics Letters,* vol. 10, No. 7, Dec. 1, 1989, pp. 693–698.

Sadowski, J. et al., "Assessing Similarity and Diversity of Combinatorial Libraries by Spatial Autocorrelation Functions and Neural Networks," *Angewandte Cheme,* vol. 34, No. 23/24, Jan. 5, 1996, pp. 2674–2677.

Thompson, L.A. and Ellman, J.A., "Synthesis and Applications of Small Molecule Libraries," *Chemical Reviews,* vol. 96, No. 1, Jan./Feb. 1996, pp. 555–600.

Barnard, John M. and Downs, Geoff M., "Computer representation and manipulation of combinatorial libraries," *Perspectives in Drug Discovery and Design,* 1997, pp. 13–30.

Brint, Andrew T. and Willett, Peter, "Upperbound procedures for the identification of similar three–dimensional chemical structures," *Journal of Computer–Aided Molecular Design,* vol. 2, No. 4, 1988, pp. 311–320.

Brown, Robert D. and Martin, Yvonne C., "Designing Combinatorial Library Mixtures Using a Genetic Algorithm" *Journal of Medicinal Chemistry,* vol. 40, No. 15, 1997, pp. 2304–2313.

Gasteiger, J. et al., "Analysis of the Reactivity of Single Bonds in Aliphatic Molecules by Statistical and Pattern Recognition Methods," *Journal of Chemical Information Computer Science,* vol. 33, No. 3, 1993, pp. 385–394.

Gillet, Valerie J. et al., "The Effectiveness of Reactant Pools for Generating Structurally–Diverse Combinatorial Libraries," *Journal of Chemical Information Computer Sciences,* vol. 37, No. 4, 1997, pp. 731–740.

Gillet, Valerie J. et al., "Selecting Combinatorial Libraries to Optimize Diversity and Physical Properties," *Journal of Chemical Information Computer Sciences,* vol. 39, No. 1, 1999, pp. 169–177.

Guez, Allon and Nevo, Igal, "Neural networks and fuzzy logic in clinical laboratory computing with application to integrated monitoring," *Clinica Chimica Acta,* 248, 1996, pp. 73–90.

Kearsley, Simon K. et al., "Chemical Similarity Using Physiochemical Property Descriptors," *Journal of Chemical Information Computer Science,* 36, 1996, pp. 118–127.

Leland, Burton A. et al., "Managing the Combinatorial Explosion," *Journal of Chemical Information Computer Science,* 37, 1997, pp. 62–70.

Lewis, Richard A. et al., "Similarity Measures for Rational Set Selection and Analysis of Combinatorial Libraries: The Diverse Property–Derived (DPD) Approach," *Journal of Chemical Information Computer Science,* 37, 1997, pp. 599–614.

Martin, Eric J. and Critchlow, Roger E., "Beyond Mere Diversity: Tailoring Combinatorial Libraries for Drug Discovery," *Journal of Combinatorial Chemistry,* vol. 1, No. 1, 1999, pp. 32–45.

Sen, K. (ed.), *Molecular Similarity I,* Springer–Verlag, 1995, pp. 1–30.

Sheridan, Robert P. et al., "Chemical Similarity Using Geometric Atom Pair Descriptors," *Journal of Chemical Information Computer Science,* 36, 1996, pp. 128–136.

Willett, Peter et al., "Chemical Similarity Searching," *Journal of Chemical Information Computer Science,* 38, 1998, pp. 983–996.

Agrafiotis, D.K., "A New Method For Analyzing Protein Sequence Relationships Based On Sammon Maps," *Protein Science,* vol. 6, No. 2, Feb. 1997, pp. 287–293.

International Search Report for Appl. No. PCT/US99/09963, 7 pages.

Amzel, L.M., "Structure–based drug design," *Current Opinion in Biotechnology,* vol. 9, No. 4, Aug. 1998, pp. 366–369.

Blaney, J.M. and Martin, E.J., "Computational approaches for combinatorial library design and molecular diversity analysis," *Current Opinion in Chemical Biology,* vol. 1, No. 1, Jun. 1997. pp. 54–59.

Brown, R.D. and Clark, D.E., "Genetic diversity: applications of evolutionary algorithms to combinatorial library design," *Expert Opinion on Therapeutic Patents,* vol. 8, No. 11, Nov. 1998, pp. 1447–1459.

Caflisch, A. and Karplus, M., "Computational combinatorial chemistry for de novo ligand design: Review and assessment," Perspectives in Drug Discovery and Design, vol. 3, 1995, pp. 51–84.

Danheiser, S.L., "Current Trends in Synthetic Peptide and Chemical Diversity Library Design," *Genetic Engineering News,* May 1, 1994, pp. 10 and 31.

Eichler, U. et al., "Addressing the problem of molecular diversity," *Drugs of the Future,* vol. 24, No. 2, 1999, pp. 177–190.

Felder, E.R. and Poppinger, D., "Combinatorial Compound Libraries for Enhanced Drug Discovery Approaches," *Advances in Drug Research,* vol. 30, 1997, pp. 112–199.

Geysen, H.M. and Mason, T.J., "Screening Chemically Synthesized Peptide Libraries for Biologically–Relevant Molecules," *Biorganic & Medicinal Chemistry Letters,* vol. 3, No. 3, 1993, pp. 397–404.

Gobbi, A. et al., "New Leads By Selective Screening of Compounds From Large Databases," *Abstracts for CINF sponsored symposia,* Apr. 17, 1997, p. 22.

Grayhill, T.L. et al., "Enhancing the Drug Discovery Process by Integration of High–Throughput Chemistry and Structure–Based Drug Design," from *Molecular Diversity and Combinatorial Chemistry: Libraries and Drug Discovery,* Chaiken and Janda (eds.), American Chemical Society, 1996, pp. 16–27.

Houghten, R.A. et al., "The Use of Synthetic Peptide Combinatorial Libraries for the Identification of Bioactive Peptides," *Peptide Research,* vol. 5, No. 6, 1992, pp. 351–358.

Klopman, G., "Artificial Intelligence Approach to Structure–Activity Studies. Computer Automated Structure Evaluation of Biological Activity of Organic Molecules," *J. Am. Chem. Soc.,* vol. 106, No. 24, Nov. 28, 1984, pp. 7315–7321.

Lajiness, M.S. et al., "Implementing Drug Screening Programs Using Molecular Similarity Methods," *QSAR: Quantitative Structure–Activity Relationships in Drug Design,* 1989, pp. 173–176.

Loew, G.H. et al., "Strategies for Indirect Computer–Aided Drug Design," *Pharmaceutical Research,* vol. 10, No. 4, 1993, pp. 475–486.

Lynch, M.F. et al., "Generic Structure Storage and Retrieval," *J. Chem. Inf. Comput. Sci.,* vol. 25, No. 3, Aug. 1985, pp. 264–270.

Myers, P.L. et al., "Rapid, Reliable Drug Discovery," *Today's Chemist At Work,* Jul./Aug. 1997, pp. 46–48, 51 & 53.

Pabo et al., "Computer–Aided Model Building Strategies for Protein Design," *Biochemistry,* vol. 25, No. 20, 1986, pp. 5987–5991.

Saudek et al., "Solution Conformation of Endothelin–1 by H NMR, CD, and Molecular Modeling," *International Journal of Peptide Protein Res.,* vol. 37, No. 3, 1991, pp. 174–179.

Saund, E., "Dimensionality–Reduction Using Connectionist Networks," *IEEE Transactions on Pattern Analysis and Machine Intelligence,* vol. 11, No. 3, Mar. 1989, pp. 304–314.

Singh, J. et al., "Application of Genetic Algorithms to Combinatorial Synthesis: A Computational Approach to Lead Identification and Lead Optimization," *J. Am. Chem. Soc.,* vol. 118, No. 7, Feb. 21, 1996, pp. 1669–1676.

Van Drie, J.H. and Lajiness, M.S., "Approaches to virtual library design," *Drug Discovery today,* vol. 3, No. 6, Jun. 1998, pp. 274–283.

Walters, W.P. et al., "Virtual screening—an overview," *Drug Discovery today,* vol. 3, No. 4, Apr. 1998, pp. 160–178.

Weber, L., "Evolutionary combinatorial chemistry: application of genetic algorithms," *Drug Discovery today,* vol. 3, No. 8, Aug. 1998, pp. 379–385.

Weber, L. et al., "Optimization of the Biological Activity of Combinatorial Compound Libraries by a Genetic Algorithm," *Angewandte Chemie International Edition in English,* vol. 34, No. 20, 1995, pp. 2280–2282.

"3DP gains drug research patent", Source of publication unclear, vol. 32, No. 1, Jan. 1996, 2 pages.

"Accelerate the Discovery Cycle with Chem–X!", Source and date of publicaton nuclear, 2 pages.

Agrafiotis, D. K., et al., "Stochastic Algorithms for Maximizing Molecular Diversity", *Journal of Chemical Information and Computer Sciences,* vol. 37, pp. 841–851, (1997).

Alsberg, B.K. et al., "Classification of pyrolysis mass spectra by fuzzy multivariate rule induction–comparison with regression, K–nearest neighbour, neural and decision–tree methods", *Analytica Chimica Acta,* vol. 348, No. 1–3, pp. 389–407, (Aug. 20, 1997).

Andrea, T.A. et al., "Applications of Neural Networks in Quantitative Structure–Activity Relationships of Dihydrofolate Reductase Inhibitors", *Journal of Medicinal Chemistry,* vol. 34, No. 9, pp. 2824–2836, (1991).

Aoyama, T. et al., "Neural Networks Applied to Quantitative Structure–Activity Relationship Analysis", *Journal of Medicinal Chemistry,* vol. 33, No. 9, pp. 2583–2590, (1990).

Aoyama, T. and Hiroshi Ichikawa, "Obtaining the Correlation Indices between Drug Activity and Structural Parameters Using a Neural Network", *Chemical & Pharmaceutical Bulletin,* vol. 39, No. 2, pp. 372–378, (1991).

"ArQule Inc", from http://www.bioportfolio.com/arqule/products.htm, 5 pages, (Mar. 18, 1998).

Baum, R.M., "Combinatorial Approaches Provide Fresh Leads for Medicinal Chemistry", *Chemical & Engineering News,* Feb. 7, 1994, (pp. 20–26).

Bentley, J. L., "Multidimensional Binary Search Trees Used for Associative Searching" *Communications of the ACM,* vol. 18, No. 9, pp. 509–517, (Sep. 1975).

Bottou, L. and Vladimir Vapnik, "Local Learning Algorithm", *Neural Computation,* vol. 4, No. 6, pp. 888–900, (Nov. 1992).

Boulu, L.G. and Gordon M. Crippen, "Voronoi Binding Site Models: Calculation of Binding Modes and Influence of Drug Binding Data Accuracy", *Journal of Computational Chemistry,* vol. 10, No. 5, pp. 673–682, (1989).

Boulu, L.G. et al., "Voronoi Binding Site Model of a Polycyclic Aromatic Hydrocarbon Binding Protein", *Journal of Medicinal Chemistry,* vol. 33, No. 2, pp. 771–775, (1990).

Brown, R. D. and Yvonne C. Martin, "Use of Structure–Activitity Data To Compare Structure–Based Clustering Methods and Descriptors for Use in Compound Selection", *Journal of Chemical Information and Computer Sciences,* vol. 36, No. 3, pp. 572–584, (1996).

Cacoullos, T., "Estimation of a Multivariate Density", *Annals of The Institute of Statistical Mathematics,* vol. 18, No. 2, pp. 179–189, (1966).

Clark, R.D., "OptiSim: An Extended Dissimilarity Selection Method for Finding Diverse Representative Subsets", *Journal of Chemical Information and Computer Sciences*. vol. 37, No. 6, pp. 1181–1188 (12 Page Internet printout), 1997.

Clark, D. E., and David R. Westhead, "Evolutionary algorithms in computer–aided molecular design", *Journal of Computer–Aided Molecular Design*, vol. 10, No. 4, pp. 337–358, (Aug. 1996).

Cramer, R. D. III et al., "Comparative Molecular Field Analyisis (CoMFA). 1. Effect of Shape on Binding of Steroids to Carrier Proteins", *Journal of The American Chemical Society*, vol. 110, No. 18, pp. 5959–5967, (Aug. 31, 1988).

Cramer, R. D. III et al., "Substructural Analysis. A Novel Approach to the Problem of Drug Design", *Journal of Medicinal Chemistry*, vol. 17, No. 5, pp. 533–535, (May 1974).

Crippen, G. M., "Voronoi binding Site Models", *Journal of Computational Chemistry*, vol. 8, No. 7, pp. 943–955, (Oct./Nov. 1987).

Friedman, J. H. et al., "An Algorithm for Finding Best Matches in Logarithmic Expected Time", *ACM Transactions on Mathematical Software*, vol. 3, No. 3, pp. 209–226, (Sep. 1977).

Friedman, J.H., "Fitting Functions To Noisy Data In High Dimensions", Department of Statistics–Stanford University Technical Report No. 101, (Aug., 1988).

Gallop, M. A. et al., "Applications of Combinatorial Technologies to Drug Discovery. 1. Background and Peptide Combinatorial Libraries", *Journal of Medicinal Chemistry*, vol. 37, No. 9, pp. 1233–1251, (Apr. 29, 1994).

Ghose, A. K. and Gordon M. Crippen, "Use of Physicochemical Parameters in Distance Geometry and Related Three–Dimensional Qantitative Structure–Activity Relationships: A Demonstration Using *Escherichia coli* Dihydrofolate Reductase Inhibitors", *Journal of Medicinal Chemistry*, vol. 28, No. 3, pp. 333–346, (1985).

Good, A. C. et al., "Structure–Activity Relationships from Molecular Similarity Matrices", *Journal of Medicinal Chemistry*, vol. 36, No. 4, pp. 433–438, (Feb. 19, 1993).

Gordon, E. M., "Applications of Combinatorial Technologies to Drug Discovery. 2. Combinatorial Organic Synthesis, Library Screening Strategies, and Future Directions", *Journal of Medicinal Chemistry*, vol. 37, No. 10, (May 13, 1994).

Hartigan, J. A., "Representation of Similarity Matrices By Trees", *Journal of the American Statistical Association*, vol. 62, No. 320, pp. 1140–1158, (Dec., 1967).

Hopfinger, A. J., "A QSAR Investigation of Dihydrofolate Reductase Inhibition by Baker Triazines based upon Molecular Shape Analysis", *Journal of the American Chemical Society*, vol. 102, No. 24, pp. 7196–7206, (Nov. 19, 1980).

Jackson, R. C., "Update on computer–aided drug design", *Current Opinion in Biotechnology*, vol. 6, No. 6, pp. 646–651, (Dec., 1995).

Kim, K. H., "Comparative molecular field analysis (CoFMA)", *Molecular Similarity in Drug Design*, ed. P. M. Dean, Blackie Academic & Professional, 1995, Ch. 12 (pp. 291–324).

Kohonen. T., "Self–Organized Formation of Topologically Correct Feature Maps", *Biological Cybernetics*, vol. 43, pp. 59–69, (1982).

Koile, K. and Richard Shapiro, "Building A Collaborative Drug Design System", *Proceedings of the 25h Hawaii International Conference on System Sciences*, pp. 706–716, (1992).

Kowalski, B. R. and C. F. Bender, "Pattern Recognition. II. Linear and Nonlinear Methods for Dsiplaying Chemical Data", *Journal of the American Chemical Society*, pp. 686–693, (Feb. 7, 1973).

Kruskal, J.B., "Nonmetric Multidimensional Scaling: A Numerical Method", *Psychometrika*, vol. 29, No. 2, pp. 115–129, (Jun., 1964).

Lengauer, T. and Matthias Rarey, "Computational methods for biomolecular docking", *Current Opinion in Structural Biology*, vol. 6, No. 3, pp. 402–406, (Jun., 1996).

Luke, B. T., "Evolutionary Programming Applied to the Development of Quantitative Structure–Activity Relationships and Quantitative Structure–Property Relationships", *Journal of Chemical Information and Computer Sciences*, vol. 34, pp. 1279–1287, (Nov./Dec., 1994).

Martin, E. J. et al., "Does Combinatorial Chemistry Obviate Computer–Aided Drug Design?", *Reviews, in Computational Chemistry*, vol. 10, pp. 75–99, (1997).

Martin, E. J. et al., "Measuring Diversity: Experimetnal Design of Combinatorial Libraries for Drug Discovery", *Journal of Medicinal Chemistry*, vol. 38, No. 9, pp. 1431–1436, (Apr. 28, 1995).

McMartin, C. and Regine S. Bohacek, "QXP: Powerful, rapid computer algorithms for structure–based drug design", *Journal of Computer–Aided Molecular Design*, vol. 11, pp. 333–344, (1997).

Mezey, P. G. and P. Duane Walker, "Fuzzy molecular fragments in drug research", *Drug Discovery Today*, vol. 2, No. 4, (Apr., 1997).

Müller, K., "On the paradigm shift from rational to random design", *Journal of Molecular Structure (Theochem)398–399*, Special Issue, pp. 467–471, (1997).

Myers, P., "The Design Of a Universal, Informer ™ Library", COMBICHEM, Inc., 10 Pages, Date unknown.

Oinuma, H. et al., "Neural Networks Applied to Structure––Activity Relationships" *Journal of Medicinal Chemistry*, vol. 33, No. 3, pp. 905–908, (1990).

Omohundro, S. M., "Bumptrees for Efficient Function, Constraint, and Classification Learning", International Computer Science Institute, pp. 693–699, Source and Date unknown.

Parrill, A. L., "Evolutionary and genetic methods in drug design", *Drug Discovery Today*, vol. 1, No. 12, pp. 514–521, (Dec., 1996).

Polanski, J., "A neural network for the simulation of biological systems", *Journal of Molecular Structure (Theochem)398–399*, Special Issue, pp. 565–571, (1997).

Ramos–Nino, M. E. et al., "A comparison of quantitative structure–activity relationships for the effect of benzoic and cinnamic acids on *Listeria monocytogenes* using multiple linear regression, artificial neural network and fuzzy systems", *Journal of Applied Microbiology*, vol. 82, No. 2, pp. 168–175, (Feb., 1997).

Rogers, D. and A. J. Hopfinger, "Application of Genetic Function Approximation to Quantitative Structure–Activity Relationships and Quantitative Structure–Property Relationships", *Journal of Chemical Information and Computer Sciences*, vol. 34, No. 4, pp. 854–866, (Jul./Aug., 1994).

Sammon, J. W., Jr., "A Nonlinear Mapping for Data Structure Analysis", *IEEE Transactions on Computers,* vol. C–18, No. 5, pp. 401–409, (May, 1969).

Simon, Z. et al., "Mapping of dihydrofolate–reductase Receptor Site by Correlation with Minimal Topological (Steric) Differences", *Journal of Theoretical Biology,* vol. 66, No. 3, pp. 485–495, (Jun. 7, 1997).

Smellie, A. S. et al., "Fast Drug–Receptor Mapping by Site–Directed Distances: A Novel Method of Predicting New Pharmacological Leads", *Journal of Chemical Information and Computer Sciences,* vol. 31, No. 3, pp. 386–392, (Aug., 1991)

Specht, D. F., "A General Regression Neural Network", *IEEE Transactions on Neural Networks,* vol. 2, No. 6, pp. 568–576, (Nov., 1991).

Svozil, D. et al., "Neural Network Prediction of the Solvatochromic Polarity/Polarizability Parameter $II^H_2$", *Journal of Chemical Information and Computer Sciences,* vol. 37, No. 2, (1997).

Todorov, N. P. and P. M. Dean, "Evaluation of method for controlling molecular scaffold diversity in de novo ligand design", *Journal of Computer–Aided Molecular Design,* vol. 11, pp. 175–192, (1997).

Torgerson, W. S., "Multidimensional Scaling: I. Theory and Method", *Psychometrika,* vol. 17, No. 4, pp. 401–419, (Dec., 1952).

Vapnik, V., "Principles of Risk Minimization for Learning Theory", *Advances in Neural Information Processing Systems 4,* pp. 831–838, Date unknown.

Vapnik, V. and L. Bottou, "Local Algorithms for Pattern Recognition and Dependencies Estimation",*Neural Computation,* vol. 5, No. 6, pp. 893–909, (Nov., 1993).

Viswanadhan, V. N. et al., "Mapping the binding site of the nucleoside transporter protein: a 3D–QSAR study", *Biochimica et Biophysica Acta,* vol. 1039, No. 3, pp. 356–366, (1990).

Warr, W. A., "Exploiting Molecular Diversity: Small Molecule Libraries for Drug Discovery", Report of Conference held in La Jolla, California, Jan. 23–25, 1995.

Westhead, D. R. et al., "A comparison of heuristic search algorithms for molecular docking", *Journal of Computer–Aided Design,* vol. 11, pp. 209–228, (1997).

Willett, P., "Genetic algorithms in molecular recognition and design" *Trends in Biotechnology,* vol., 13, No. 12, pp. 516–521, (Dec., 1995).

Willett, P. and Vivienne Winterman, "A Comparison of Some Measures for the Determination of Inter–Molecular Structural Similarity Measures of Inter–Molecular Structural Similarity",*Quantitative Structure–Activity Relationships,* vol. 5, No. 1, pp. 18–25, (Mar., 1986).

Zadeh, L. A., "Communication Fuzzy Algorithms", *Information and Control,* vol. 12, No. 2, pp. 94–102, (Feb., 1968).

Zadeh, L. A., "Fuzzy Sets", *Information and Control,* vol. 8, No. 3, pp. 338–353, (Jun., 1965).

Copy of International Search Report issued May 13, 1998 for PCT/US97/20918.

Copy of International Search Report issued Apr. 21, 1998 for PCT/US97/20919.

\* cited by examiner

METHOD, SYSTEM, AND COMPUTER PROGRAM PRODUCT FOR REPRESENTING SIMILARITY/DISSIMILARITY BETWEEN CHEMICAL COMPOUNDS

CROSS REFERENCE TO RELATED APPLICATIONS

This application is related to and claims priority to U.S. Provisional Application Ser. No. 60/030,187, filed Nov. 4, 1996, titled "Stochastic Algorithms for Maximizing Molecular Diversity," which is herein incorporated by reference in its entirety. This application is related to U.S. application Ser. No. 08/963,870, filed Nov. 4, 1997, titled, "System, Method And Computer Program Product For Identifying Chemical Compounds Having Desired Properties," which is herein incorporated by reference in its entirety.

BACKGROUND OF THE INVENTION

1. Field of the Invention

The present invention is generally directed to displaying and processing data using a computer, and more particularly directed to visualizing and interactive processing chemical compounds using a computer.

2. Related Art

Currently, research to identify chemical compounds with useful properties (such as paints, finishes, plasticizers, surfactants, scents, drugs, herbicides, pesticides, veterinary products, etc.) often includes the synthesis/acquisition and analysis of large libraries of chemical compounds. More and more, combinatorial chemical libraries are being synthesized/acquired and analyzed to conduct this research.

A combinatorial chemical library is a collection of diverse chemical compounds generated by either chemical synthesis or biological synthesis by combining a number of chemical "building blocks" such as reagents. For example. a linear combinatorial chemical library such as a polypeptide library is formed by combining a set of chemical building blocks called amino acids in every possible way for a given compound length (i.e., the number of amino acids in a polypeptide compound). Millions of chemical compounds theoretically can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al., "Applications of Combinatorial Technologies to Drug Discovery, Background and Peptide Combinatorial Libraries, " J. Med. Chem. 37, 1233–1250 (1994)).

Advanced research in this area often involves the use of directed diversity 486 libraries. A directed diversity library is a large collection of chemical compounds having properties/features/characteristics that match some prescribed properties. The generation, analysis, and processing of directed diversity libraries are described in U.S. Pat. Nos. 5,463,564; 5,574,656; and 5,684,711, and pending U.S. application titled "SYSTEM, METHOD AND COMPUTER PROGRAM PRODUCT FOR IDENTIFYING CHEMICAL COMPOUNDS HAVING DESIRED PROPERTIES," all of which are herein incorporated by reference in their entireties.

In conducting such research, it would be very valuable to be able to compare the properties, features, and other identifying characteristics of compounds. For example, suppose that a researcher has identified a compound X that exhibits some useful properties. It would aid the researcher greatly if he could identity similar compounds, since those similar compounds might also exhibit those same useful properties.

It would also help a researcher in his work to be able to easily synthesize compounds, or retrieve compounds from a chemical inventory. Further, it would greatly aid a researcher to be able to interactively analyze and otherwise process chemical compounds.

SUMMARY OF THE INVENTION

Briefly stated, the present invention is directed to a system method, and computer program product for visualizing and interactively analyzing data relating to chemical compounds. The invention operates as follows. A user selects a plurality of compounds to map, and also selects a method for evaluating similarity/dissimilarity between the selected compounds. A non-linear map is generated in accordance with the selected compounds and the selected method. The non-linear map has a point for each of the selected compounds, wherein a distance between any two points is representative of similarity/dissimilarity between the corresponding compounds. A portion of the non-linear map is then displayed. Users are enabled to interactively analyze compounds represented in the non-linear map.

Further features and advantages of the present invention, as well as the structure and operation of various embodiments of the present inventions are described in detail below with reference to the accompanying drawings. In the drawings, like reference numbers indicate identical or functionally similar elements. Also, the leftmost digit(s) of the reference numbers identify the drawings in which the associated elements are first introduced.

BRIEF DESCRIPTION OF THE FIGURES

The present invention will be described with reference to the accompanying drawings, wherein.

DETAILED DESCRIPTION OF THE PREFERRED EMBODIMENTS

Table of Contents

1. Overview of the Present Invention
2. Structure of the Invention
3. Implementation Embodiment of the Invention
4. Overview of Multidimensional Scaling (MDS) and Nonlinear Mapping (NLM)
    4.1 Procedure Suitable for Relatively Small Data Sets
    4.2 Procedure Suitable for Large Data Sets
5. Evaluation Properties (Features) and Distance Measures
    5.1 Evaluation Properties Having Continuous or Discrete Real Values
    5.2 Distance Measure Where Values of Evaluation Properties Are Continuous or Discrete Real Numbers
    5.3 Evaluation Properties Having Binary Values
    5.4 Distance Measures Where Values of Evaluation Properties Are Binary
6. Scaling of Evaluation Properties
7. Improvements to Map Generation Process
    7.1 Pre-Ordering
    7.2 Localized Refinement
    7.3 Incremental Refinement
8. Operation of the Present Invention
9. User Interface of the Present Invention
    9.1 Structure Browser
    9.2 Map Viewer
    9.3 Interactivity of the Present Invention
        9.3.1 Map Viewer as Target
        9.3.2 Map Viewer as Source
    9.4 Multiple Maps
10. Examples

1. OVERVIEW OF THE PRESENT INVENTION

The present invention is directed to a computer-based system, method, and/or computer program product for visualizing and analyzing chemical data using interactive multidimensional (such as 2- and/or 3-dimensional) non-linear maps. In particular, the invention employs a suite of non-linear mapping algorithms to represent chemical compounds as objects in preferably 2D or 3D) Euclidean space.

According to the invention, the distances between objects in that space represent the similarities and/or disgimilaritieq of the corresponding compounds (relative to selected properties or features of the compounds) computed by some prescribed method. The resulting maps are displayed on a suitable graphics device (such as a graphics terminal, for example), and interactively analyzed to reveal relationships between the data, and to initiate an array of tasks related to these compounds.

2. STRUCTURE OF THE INVENTION

Figure 1:
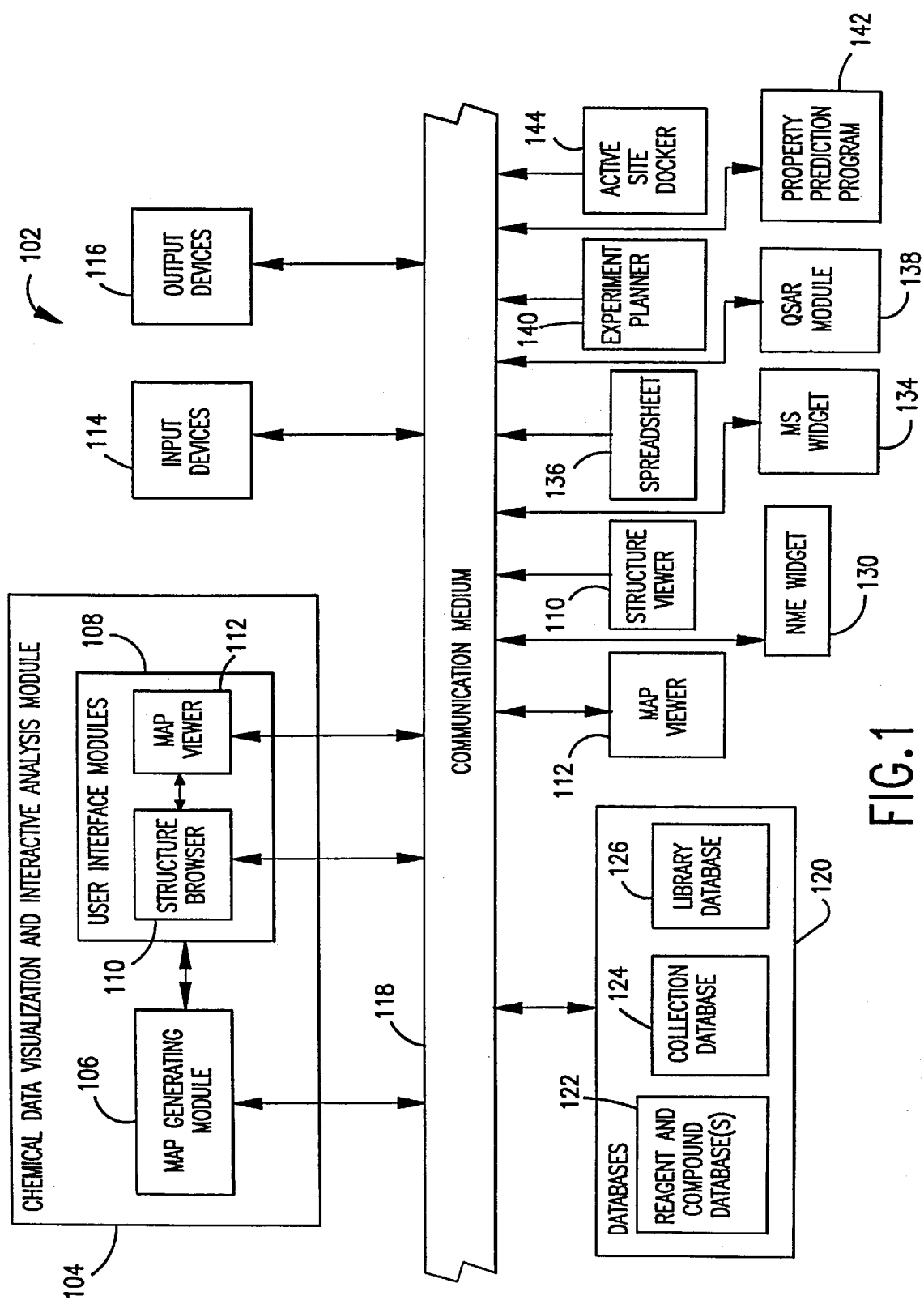
FIG. 1 illustrates a block diagram of a computing environment according to an embodiment of the invention.

FIG. 1 is a block diagram of a computing environment 102 according to a preferred embodiment of the present invention.

A chemical data visualization and interactive analysis module 104 includes a map generating module 106 and user interface modules 108. The map generating module 106 determines distances between chemical compounds relative to one or more selected properties or features (herein sometimes called evaluation properties or features) of the compounds. The map generating module 106 performs this function by retrieving and analyzing data on chemical compounds and reagents from reagent and compound databases 122. These reagent and compound databases 122 store information on chemical compounds and reagents of interest.

The reagent and compound databases 122 are part of databases 120, which communicate with the chemical data visualization and interactive analysis module 104 via a communication medium 118. The communication medium 118 is preferably any type of data communication means, such as a data bus, a computer network, etc.

The user interface modules 108, which include a map viewer 112 and optionally a structure browser 110, displays a preferably 2D or 3D non-linear map on a suitable graphics device. The non-linear map includes objects that represent the chemical compounds, where the distances between the objects in the non-linear map are those distances determined by the map generating module 106. The user interface modules 108 enable human operators to interactively analyze and process the information in the non-linear map so as to reveal relationships between the data, and to initiate an array of tasks related to the corresponding compounds.

The user interface modules 108 enable users to organize compounds as collections (representing, for example, a combinatorial library). Information pertaining to compound collections are preferably stored in a collection database 124. Information on reagents that are mixed to form compound collections are preferably stored in a library database 126.

Input Device(s) 114 receive input (such as data, commands, queries, etc.) from human operators and forward such input to, for example, the chemical data visualization and interactive analysis module 104 via the communication medium 118. Any well known, suitable input device can be used in the present invention, Such as a keyboard, pointing device (mouse, roller ball, track ball, light pen, etc.), touch screen, voice recognition, etc. User input can also be stored and then retrieved. as appropriate, from data/command files.

Output Device(s) 116 output information to human operators. Any well known, suitable output device can be used in the present invention, such as a monitor, a printer, a floppy disk drive or other storage device, a text-to-speech synthesizer, etc.

As described below, the present invention enables the chemical data visualization and interactive analysis module 104 to interact with a number of other modules, including but not limited to one or more map viewers 112. NMR (nuclear magnetic resonance) widget/module 130. structure viewers 110, MS (mass spectrometry) widget/module 134, spreadsheets 136, QSAR (Quantitative Structure-Activity Relationships) module 138, an experiment planner 140, property prediction programs 142, active site docker 144, etc. These modules communicate with the chemical data visualization and interactive analysis module 104 via the communication medium 118.

3. IMPLEMENTATION EMBODIMENT OF THE INVENTION

Figure 2:
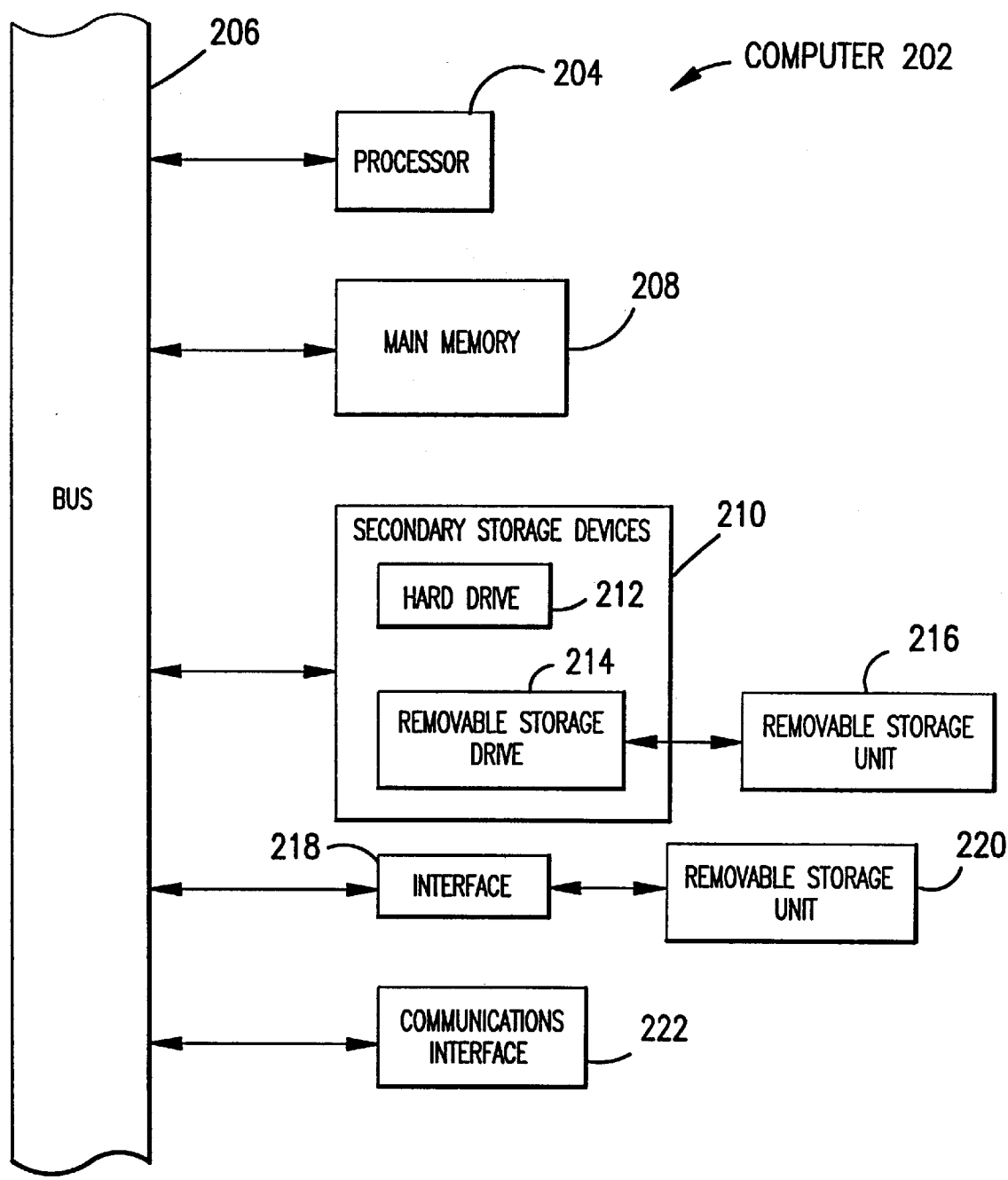
FIG. 2 is a block diagram of a computer useful for implementing components of the invention.

Components shown in the computing environment 102 of FIG. 1 (such as the chemical data visualization and interactive analysis module 104) can be implemented using one or more computers, such as an example computer 202 shown in FIG. 2.

The computer 202 includes one or more processors, such as processor 204. Processor 204 is connected to a communication bus 206. Various software embodiments are described in terms of this example computer system. After reading this description, it will become apparent to a person skilled in the relevant art(s) how to implement the invention using other computer systems and/or computer architectures.

Computer 202 also includes a main memory 208, preferably random access memory (RAM), and can also include one or more secondary storage devices 210. Secondary storage devices 210 can include, for example, a hard disk drive 212 and/or a removable storage drive 214, representing a floppy disk drive, a magnetic tape drive, an optical disk drive, etc. Removable storage drive 214 reads from and/or writes to a removable storage unit 216 in a well known manner. Removable storage unit 216 represents a floppy disk, magnetic tape, optical disk, etc. which is read by and written to by removable storage drive 214. Removable storage unit 216 includes a computer usable storage medium having stored therein computer software and/or data.

In alternative embodiments, the computer 202 can include other similar means for allowing computer programs or other instructions to be loaded into computer 202. Such means can include, for example, a removable storage unit 220 and an interface 218. Examples of such can include a program cartridge and cartridge interface (such as that found in video game devices), a removable memory chip (such as an EPROM, or PROM) and associated socket, and other removable storage units 220 and interfaces 218 which allow software and data to be transferred from the removable storage unit 220 to computer 202.

The computer 202 can also include a communications interface 222. Communications interface 222 allows software and data to be transferred between computer 202 and external devices. Examples of communications interface 222 include, but are not limited to a modem, a network interface (such as an Ethernet card), a communications port, a PCMCIA slot and card, etc. Software and data transferred via communications interface 222 are in the form of signals which can be electronic, electromagnetic, optical or other signals capable of being received by communications interface 222.

In this document, the term "computer program product" is used to generally refer to media such as removable storage units 216, 220, a hard drive 212 that can be removed from the computer 202, and signals carrying software received by the communications interface 222. These computer program products are means for providing software to the computer 202.

Computer programs (also called computer control logic) are stored in main memory and/or secondary storage devices 210. Computer programs can also be received via communications interface 222. Such computer programs, when executed, enable the computer 202 to perform the features of the present invention as discussed herein. In particular, the computer programs, when executed, enable the processor 204 to perform the features of the present invention. Accordingly, such computer programs represent controllers of the computer 202.

In an embodiment where the invention is implemented using, software, the software can be stored in a computer program product and loaded into computer 202 using removable storage drive 214, hard drive 212, and/or communications interface 222. The control logic (software), when executed by the processor 204, causes the processor 204 to perform the functions of the invention as described herein.

In another embodiment, the automated portion of the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using, a combination of both hardware and software.

The computer 202 can be any suitable computer, such as a computer system running an operating system supporting a graphical user interface and a windowing environment. A suitable computer system is a Silicon Graphics, Inc. (SCI) workstation/server, a Sun workstation/server, a DEC workstation/server, an IBM workstation/server, an IBM compatible PC, an Apple Macintosh, or any other suitable computer system, such as one using one or more processors from the Intel Pentium family, such as Pentium Pro or Pentium II. Suitable operating systems include, but are not limited to, IRIX, OS/Solaris, Digital Unix, AIX, Microsoft Windows 95/NT. Apple Mac OS, or any other operating system supportino a graphical user interface and a windowing environment. For example, in a preferred embodiment the program may be implemented and run on an Silicon Graphics Octane workstation running the IRIX 6.4 operating system, and using the Motif graphical user interface based on the X Window System.

4. OVERVIEW OF MULTIDIMENSIONAL SCALING (MDS) AND NON-LINEAR MAPPING (NLM)

According to the present invention, multidimensional scaling (MDS) and non-linear mapping (NLM) techniques are used to generate the non-linear map (i.e., the non-linear map) that includes objects, where the objects represent chemical compounds, and the distances between the objects are indicative ot the similarities and dissimilarities between the corresponding compounds. MDS and NLM are described in this section.

MDS and NLM were introduced by Torgerson, *Phychometrika*, 17:401 (1952); Kruskal, *Psychometrika*, 29:115 (1964); and Sammon, *IEEE Trans. Comput.*, C-18:401 (1969) as a means to generate low-dimensional representations of psychological data. Multidimensional scaling and non-linear mapping are reviewed in Schiffman, Reynolds and Young, *Introduction to Multidimensional Scaling*, Academic Press, New York (1981); Young and Hamer, *Multidimensional Scaling: History, Theory and Applications*, Erlbaum Associates, Inc., Hillsdale. N.J. (1987); and Cox and Cox, *Multidimensional Scaling*, Number 59 in *Monographs in Statistics and Applied Probability*, Chapman-Hall (1994). The contents of these publications are incorporated herein by reference in their entireties.

4.1 PROCEDURE SUITABLE FOR RELATIVELY SMALL DATA SETS

MDS and NLM (these are generally the same, and are hereafter collectively referred to as MDS) represent a collection of methods for visualizing proximity relations of objects by distances of points in a low-dimensional Euclidean space. Proximity measures are reviewed in Hartigan, *J.*

*Am. Statist. Ass.*, 62:1140 (1967). which is incorporated herein by reference in its entirety. In particular, given a finite set of vectorial or other samples A={$a_i$, i=1, ..., k}, a distance function $d_{ij}$=d($a_i$, $a_j$), with $a_i$, $a_j \in$ A, which measures the similarity and dissimilarity between the i-th and j-th objects in A, and a set of images X={$x_i$, ..., $x_k$; $x_i \in {}^m\Re$} of A on an m-dimensional display plane ($\Re^m$ being an m dimensional vector of real numbers), the objective is to place $x_i$ onto the display plane in such a way that their Euclidean distances $\|x_i - x_j\|$ approximate as closely as possible the corresponding values $d_{ij}$. This projection, which can only be made approximately, is carried out in an iterative fashion by minimizing an error function which measures the difference between the distance matrices of the original and projected vector sets. Several such error functions have been proposed, most of which are of the least-squares type, including Kruskal's 'stress':

$$S = \sqrt{\frac{\sum_{i<j}^{k} (d_{ij} - \delta_{ij})^2}{\sum_{i<j}^{k} d_{ij}^2}} \qquad \text{EQ. 1}$$

Sammon's error criterion:

$$E = \frac{\sum_{i<j}^{k} \frac{(d_{ij} - \delta_{ij})^2}{d_{ij}}}{\sum_{i<j}^{k} d_{ij}} \qquad \text{EQ. 2}$$

and Lingoes' alienation coefficient:

$$K = \sqrt{\frac{\sum_{i<j}^{k} (d_{ij} \delta_{ij})^2}{\sum_{i<j}^{k} \delta_{ij}}} \qquad \text{EQ. 3}$$

where $\delta_{ij} = \|x_i - x_j\|$ is the Euclidean distance between the images $x_i$ and $x_j$ on the display plane. Generally, the solution is found in an iterative fashion by (1) computing or retrieving from a database the distances $d_{ij}$; (2) initializing the images $x_i$; (3) computing the distances of the images $\delta$ and the value of the error function (e.g. S, E or K in EQ. 1–3 above); (4) computing a new configuration of the images $x_i$ using a gradient descent procedure, such as Kruskal's linear regression or Guttman's rank-image permutation; and (5) repeating steps 3 and 4 until the error is minimized within some prescribed tolerance.

For example, the Sammon algorithm minimizes EQ. 2 by iteratively updating the coordinates $x_i$ using Eq 4:

$$x_{pq}(m+1) = x_{pq}(m) - \lambda \Delta_{pq}(m) \qquad \text{EQ. 4}$$

where m is the iteration number, $x_{pq}$ is the q-th coordinate of the p-th image $x_p \lambda$ is the learning rate and $$\Delta_{pq}(m) = \frac{\frac{\partial E(m)}{\partial x_{pq}(m)}}{\left| \frac{\partial^2 E(m)}{\partial x_{pq}(m)^2} \right|} \qquad \text{EQ. 5}$$

The partial derivatives in EQ. 5 are given by:

$$\frac{\partial E(m)}{\partial x_{pq}(m)} = -2 \frac{\sum_{j=1, j \neq p}^{k} \frac{d_{pj} - \delta_{pj}}{d_{pj} \delta_{pj}} (x_{pq} - x_{jq})}{\sum_{i<j}^{k} d_{ij}} \qquad \text{EQ. 6}$$

$$\frac{\partial^2 E(m)}{\partial x_{pq}(m)^2} = \\ -2 \frac{\sum_{i<j}^{k} \frac{1}{d_{pj} \delta_{pj}} \left[ (d_{pj} - \delta_{pj}) - \frac{(x_{pq} - x_{jq})^2}{\delta_{pj}} \left( 1 + \frac{(d_{pj} - \delta_{pj})}{\delta_{pj}} \right) \right]}{\sum_{i<j}^{k} d_{ij}} \qquad \text{EQ. 7}$$

The non-linear mapping is obtained by repeated evaluation of EQ. 2, followed by modification of the coordinates using EQ. 4 and 5, until the error is minimized within a prescribed tolerance.

4.2 PROCEDURE SUITABLE FOR LARGE DATA SETS

The general refinement paradigm described in Section 4.1 is suitable for relatively small data sets, but has one important limitation that renders it impractical for large data sets. This limitation stems from the fact that the computational effort required to compute the gradients scales to the square of the size of the data set. For relatively large data sets, this quadratic time complexity makes even a partial refinement intractable.

According to the present invention, the following approach is used for large data sets. This approach is to use iterative refinement based on 'instantaneous' errors. As in the approach described in Section 4.1, this approach of Section 4.2 starts with an initial configuration of points generated at random or by some other procedure (as described below in Section 7). This initial configuration is then continuously refined by repeatedly selecting two points i, j, at random, and modifying their coordinates on the non-linear map according to Eq. 8:

$$x_i(t+1) = f(t, x_i(t), x_j(t), d_{ij}) \qquad \text{EQ. 8}$$

where t is the current iteration, $x_i(t)$ and $x_j(t)$ are the current coordinates of the i-th and j-th points on the non-linear map, $x_i(t+1)$ are the new coordinates of the i-th point on the non-linear map, and $d_{ij}$ is the true distance between the i-th and j-th points that we attempt to approximate on the non-linear map (see above). f(.) in EQ. 8 above can assume any functional form. Ideally, this function should try to minimize the difference between the actual and target distance between the i-th and j-th points. For example,f(.) may be given by EQ. 9:

$$x_i(t+1) = f(t, x_i(t), x_j(t), d_{ij}) \qquad \text{EQ. 9}$$
$$= x_i(t) + 0.5 \lambda(t) \frac{(d_{ij} - \delta_{ij}(t))}{\delta_{ij}(t)} (x_i(t) - x_j(t))$$

where t is the iteration number, $\delta_{ij} = \|x_i(t) - x_j(t)\|$, and $\lambda(t)$ is an adjustable parameter, referred to hereafter as the 'learning rate.'

An analogous equation has been suggested by Kohonen for the training of self-organizing maps (Kohonen, *Self-Organizing Maps*, Springer-Verlag. Berlin (1995)), incorporated herein by reference in its entirety. This process is repeated for a fixed number of cycles, or until some global error criterion is minimized within some prescribed tolerance. A large number of iterations are typically required to achieve statistical accuracy.

The method described above is generally reminiscent of Kohonen's self-organizing principle (Kohonen, *Biological Cybernetics*, 43:59 (1982)) and neural network back-propagation training (Werbos, *Beyond Regression: New Tools for Prediction and Analysis in the Behavioral Sciences*, PhD Thesis, Harvard University, Cambridge, Mass. (1974)), and Rumelhart and McClelland, Eds., *Parallel Distributed Processing: Explorations in the Microstructure of Cognition*, Vol. 1, MIT Press. Cambridge, Mass. (1986)), all of which are incorporated herein by reference in their entireties.

The learning rate $\lambda(t)$ in EQ. 9 plays a key role in ensuring convergence. If $\lambda$ is too small, the coordinate updates are small, and convergence is slow. If, on the other hand, $\lambda$ is too large, the rate of learning may be accelerated, but the non-linear map may become unstable (i.e. oscillatory). Typically, $\lambda$ ranges in the interval [0, 1] and may be fixed, or it may decrease monotonically during the refinement process. Moreover, $\lambda$ may also be a function of i, j and/or $d_{ij}$, and can be used to apply different weights to certain objects, distances and/or distance pairs. For example, $\lambda$ may be computed by EQ. 10:

$$\lambda(t) = \left(\lambda_{max} + t\frac{\lambda_{min} - \lambda_{max}}{T}\right)\frac{1}{1+ad_{ij}} \quad \text{EQ. 10}$$

or EQ. 11:

$$\lambda(t) = \left(\lambda_{max} + t\frac{\lambda_{min} - \lambda_{max}}{T}\right)e^{-ad_{ij}} \quad \text{EQ. 11}$$

where $\lambda_{max}$ and $\lambda_{min}$ are the (unweighted) starting and ending learning rates such that $\lambda_{max}, \lambda_{min} \in [0,1]$, T is the total number of refinement steps (iterations), t is the Current iteration number, and $\alpha$ is a constant scaling factor. EQ. 10 and 11 have the effect of decreasing the correction at large separations, thus creating a noni-linear map which preserves shot-range interactions more faithfully than long-range ones. Weighting is discussed in greater detail below. Because of the general resemblance of the training process described above to Kohonen's self-organizing principle. these maps shall sometimes be herein called 'Self-Organizing Nonlinear Maps.'

One of the main advantages of this approach is that it makes partial refinements possible. It is often sufficient that the pair-wise dissimilarities are represented only approximately to reveal the general structure and topology of the data. Unlike traditional MDS, this approach allows very fine control of the refinement process. Moreover, as the non-linear map self-organizes, the pair-wise refinements become cooperative, which partially alleviates the quadratic nature of the problem. The general usefulness of multi-dimensional scaling stems from the fact that data in $R^d$ are almost never d-dimensional. Although scaling becomes more problematic as the true dimensionality of the space increases, the presence of structure in the data is very frequently reflected on the resulting map. Of course, one can easily conceive of situations where MDS is not effective, particularly when the data is random and truly hyper-dimensional. Fortunately, these situations rarely arise in practice, as some form of structure is always present in the data, particularly data related to molecular structure and function.

The embedding procedure described above does not guarantee convergence to the global minimum (i.e., the most faithful embedding in a least-squares sense). It so desired, the refinement process may be repeated a number of times from different starting configurations and/or random number seeds. It should also be pointed out that the absolute coordinates in the non-linear map carry no physical significance. What is important are the relative distances between points, and the general structure and topology of the data (presence, density and separation of clusters, etc.).

The method described above is ideally suited for both metric and non-metric scaling. The latter is particularly useful when the (dis)similarity measure is not a true metric, i.e. it does not obey the distance postulates and, in particular, the triangle inequality (such as the Tanimoto coefficient, for example). Although an 'exact' projection is only possible when the distance matrix is positive definite, meaningful projections can still be obtained even when this criterion is not satisfied. As mentioned above, the overall quality of the projection is determined by a sum-of-squares error function such as those shown in EQ. 1–3.

5. EVALUATION PROPERTIES (FEATURES) AND DISTANCE MEASURES

As mentioned above, the distances $d_{ij}$ between chemical compounds are computed according to some prescribed measure of molecular 'similarity'. This similarity can be based on any combination of properties or features of the compounds. For example, the similarity measure may be based on structural similarity, chemical similarity, physical similarity, biological similarity, and/or some other type of similarity measure which can be derived from the structure or identity of the compounds. Under the system of the present invention, any similarity measure can be used to construct the non-linear map. The properties or features that are being used to evaluate similarity or dissimilarity among compounds are sometimes herein collectively called "evaluation properties."

5.1 EVALUATION PROPERTIES HAVING CONTINUOUS OR DISCRETE REAL VALUES

As noted above, in a preferred embodiment of the present invention, the similarity measure may be derived from a list of physical, chemical and/or biological properties (i.e., evaluation properties) associated with a set of compounds. Under this formalism, the compounds are represented as vectors in multi-variate property space, and their similarity may be computed by some geometrical distance measure.

In a preferred embodiment, the property space is defined using one or more molecular features (descriptors). Such molecular features may include topological indices, physicochemical properties, electrostatic field parameters, volume and surface parameters, etc. For example, these features may include, but are not limited to, molecular volume and surface areas, dipole moments, octanol-water partition coefficients, molar refractivities, heats of formation, total energies, ionization potentials, molecular connectivity indices, 2D and 3D auto-correlation vectors, 3D structural and/or pharmacophoric parameters, electronic fields, etc. However, it should be understood that the present invention is not limited to this embodiment. For example, molecular features may include the observed biological activities of a set of compounds against an array of biological targets such as enzymes or receptors (also known as affinity fingerprints). In fact, any vectorial representation of chemical data can be used in the present invention.

5.2 DISTANCE MEASURE WHERE VALUES OF EVALUATION PROPERTIES ARE CONTINUOUS OR DISCRETE REAL NUMBERS

A "distance measure" is some algorithm or technique used to determine the difference between compounds based on the selected evaluation properties. The particular distance measure that is used in any given situation depends, at least in part, on the set of values that the evaluation properties can take.

For example, where the evaluation properties can take real numbers as values, then a suitable distance measure is the Minkowski metric, shown in EQ. 12:

$$d_{ij} = d(x_i, x_j) = \left(\sum_k |x_{ik} - x_{jk}|^r\right)^{\frac{1}{r}} \qquad \text{EQ. 12}$$

where k is used to index the elements of the property vector, and r∈[1, ∞). For r=1.0, E.Q. 12 is the city-block or Manhattan metric. For r=2.0, EQ. 12 is the ordinary Euclidean metric. For r=∞, EQ. 12 is the maximum of the absolute coordinate distances, also referred to as the 'dominance' metric, the 'sup' metric, or the 'ultrametric' distance. For any value of r∈[1, ∞), it can be shown that the Minkowski metric is a true metric, i.e. it obeys the distance postulates and, in particular, the triangle inequality.

5.3 EVALUATION PROPERTIES HAVING BINARY VALUE

Alternatively, the evaluation properties of the compounds may be represented in a binary form (i.e., either a compound has or does not have an evaluation property), where each bit is used to indicate the presence or absence (or potential presence or absence) of some molecular feature or characteristic. For example, compounds may be encoded using substructure keys where each bit is used to denote the presence or absence of a specific structural feature or pattern in the target molecule. Such features include, but are not limited to, the presence, absence or minimum number of occurrences of a particular element (e.g. the presence of at least 1, 2 or 3 nitrogen atoms), unusual or important electronic configurations and atom types (e.g. doubly-bonded nitrogen or aromatic carbon), common functional groups such as alcohols amines etc, certain primitive and composite rings, a pair or triplet of pharmacophoric groups at a particular separation in 3-dimensional space, and 'disjunctions' of unusual features that are rare enough not to worth an individual bit, yet extremely important when they do occur (typically, these unusual features are assigned a common bit that is set if any one of the patterns is present in the target molecule).

Alternatively, the evaluation properties of compounds may be encoded in the form of binary fingerprints, which do not depend on a predefined fragment or feature dictionary to perform the bit assignment. Instead, every pattern in the molecule up to a predefined limit is systematically enumerated, and serves as input to a hashing algorithm that turns 'on' a small number of bits at pseudo-random positions in the bitmap. Although it is conceivable that two different molecules may have exactly the same fingerprint, the prob-ability of this happening is extremely small for all but the simplest cases. Experience suggests that these fingerprints contain sufficient information about the molecular structures to permit meaningful similarity comparisons.

5.4 DISTANCE MEASURES WHERE VALUES OF EVALUATION PROPERTIES ARE BINARY

A number of similarity (distance) measures can be used with binary descriptors (i.e., where evaluation properties are binary or binary fingerprints). The most frequently used ones are the normalized Hamming distance:

$$H = \frac{|XOR(x, y)|}{N} \qquad \text{EQ. 13}$$

which measures the number of bits that are different between x and y, the Tanimoto or Jaccard coefficient:

$$T = \frac{|AND(x, y)|}{|IOR(x, y)|} \qquad \text{EQ. 14}$$

which is a measure of the number of substructures shared by two molecules relative to the ones they could have in common, and the Dice coefficient:

$$D = \frac{2|AND(x, y)|}{|x| + |y|} \qquad \text{EQ. 15}$$

In the equations listed above, AND(x, y) is the intersection of binary sets x and y (bits that are 'on' in both sets), IOR(x, y) is the union or 'inclusive or' of x and y (bits that are 'on' in either x or y), XOR is the 'exclusive or' of x and y (bits that are 'on' in either x or y, but not both), |x| is the number of bits that are 'on' in x, and N is the length of the binary sets measured in bits (a constant).

Another popular metric is the Euclidean distance which, in the case of binary sets, can be recast in the form:

$$E = \sqrt{N - |XOR(x, NOT(y))|a} \qquad \text{EQ. 16}$$

where NOT(y) denotes the binary complement of y. The expression |XOR(x, NOT(y))| represents the number of bits that are identical in x and y (either 1's or 0's). The Euclidean distance is a good measure of similarity when the binary sets are relatively rich, and is mostly used in situations in which similarity is measured in a relative sense.

In the examples described above, the distance between two compounds is determined using a binary or multivariate representation. However, the system of the present invention is not limited to this embodiment. For example, the similarity between two compounds may be determined by comparing the shapes of the molecules using a suitable 3-dimensional alignment method, or it may be inferred by a similarity model defined according to a prescribed procedure. For example, one such similarity model may be a neural network trained to predict a similarity coefficient given a suitably encoded pair of compounds. Such a neural network may be trained using a training set of structure pairs and a known similarity coefficient for each Such pair, as determined by user input, for example.

6. SCALING OF EVALUATION PROPERTIES

Referring back to EQ. 12, according to the present invention, the features (i.e., evaluation properties) may be scaled differently to reflect their relative importance in assessing the proximity between two compounds. For example, suppose the user has selected two evaluation properties, Property A and Property B. It Property A has a weight of 2, and Property B has a weight of 10, then Property B will have five times the impact on the distance calculation than Property A.

According to this embodiment of the invention, EQ. 12 may be replaced by EQ 17:

$$d_{ij} = d(x_i, x_j) = \left(\sum_k (w_k|x_{ik} - x_{jk}|)^r\right)^{\frac{1}{r}} \quad \text{EQ. 17}$$

where $w_k$ is the weight of the k-th property. An example of such a weighting factor is a normalization coefficient. However, other weighting schemes may also be used.

According to the present invention, the scaling (weights) need not be uniform throughout the entire map, i.e. the resulting map need not be isomorphic. Hereafter maps derived from uniform weights shall be referred to as globally weighted (isomorphic), whereas maps derived from non-uniform weights shall be referred to as locally weighted (non-isomorphic). On locally-weighted maps, the distances on the non-linear map reflect a local measure of similarity. That is, what determines similarity in one domain of the non-linear map is not necessarily the same with what determines similarity on another domain of the non-linear map. For example, locally-weighted maps may be used to reflect similarities derived from a locally-weighted case-based learning algorithm. Locally-weighted learning uses locally weighted training to average, interpolate between, extrapolate from, or otherwise combine training data. Most learning methods (also referred to as modeling or prediction methods) construct a single model to fit all the training data. Local models, on the other hand, attempt to fit the training data in a local region around the location of the query. Examples of local models include nearest neighbors, weighted average, and locally weighted regression. Locally-weighted learning is reviewed in Vapnik, in *Advances in Neural Information Processing Systems*, 4:831, Morgan-Kaufman, San Mateo, Calif. (1982); Bottou and Vapnik, *Neural Computation*, 4(6):888 (1992); and Vapnik and Bottou, *Neural Computation*, 5(6):893 (1993), all of which are incorporated herein by reference in their entireties.

According to the present invention, it is also possible to construct a poll-linear map from a distance matrix which is not strictly symmetric, i.e. a distance matrix where $d_{ij} \neq d_{ji}$. A potential use of this approach is in situations where the distance function is defined locally, e.g. in a locally weighted model using a point-based local distance function. In this embodiment, each training case has associated with it a distance function and the values of the corresponding parameters. Preferably, to construct a non-linear map which reflects these local distance relationships, the distance between two points is evaluated twice, using the local distance functions of the respective points. The resulting distances are averaged, and are used as input in the non-linear mapping algorithm described above. If the point-based local distance functions vary in some continuous or semi-continuous fashion throughout the feature space, this approach could potentially lead to a meaningful projection.

7. IMPROVEMENTS TO MAP GENERATION PROCESS

This section describes improvements to the chemical visualization tap generation process described above. Each of the enhancements described below is under the control of the user. That is, the user can elect to perform or not perform each of the enhancements discussed below. Alternatively, the invention can be defined so that the below enhancements are automatically performed, unless specifically overridden by the user (or in some embodiments, the user may not have the option of overriding one or more of the below enhancements).

7.1 PRE-ORDERING

In many eases, the approach described above for generating the non-linear map may be accelerated by pre-ordering, the data using a suitable statistical method. For example, if the data is available in vectorial or binary form, the initial configuration of the points on the non-linear map may be computed using Principal Component Analysis. In a preferred embodiment, the initial configuration may be constructed from the first 3 principal components of the feature matrix (i.e. the 3 latent variables which account for most of the variance in the data). In practice, this technique can have profound effects in the speed of refinement. Indeed, if a random initial configuration is used. a significant portion of the training time is spent establishing the general structure and topology of the non-linear map, which is typically characterized by large rearrangements. If, on the other hand, the input configuration is partially ordered, the error criterion can be reduced relatively rapidly to an acceptable level.

7.2 LOCALIZED REFINEMENT

If the data is highly clustered, by virtue of the sampling process low-density areas may be refined less effectively than high-density areas. In a preferred embodiment, this tendency may be partially compensated by a modification to the original algorithm which increases the sampling probability in low-density areas. In one embodiment, the center of mass of the non-linear map is identified, and concentric shells centered at that point are constructed. A series of regular refinement iterations are then carried out, each time selecting points from within or between these shells. This process is repeated for a prescribed number of cycles. This phase is then followed by a phase of regular refinement using global sampling, and the process is repeated.

As mentioned above, the basic algorithm does not distinguish short- from long-range distances. EQ. 10 and 11 describe a method to ensure that short-range distances are preserved more faithfully than long-range ones through the use of weighting. An alternative (and complementary) approach is to ensure that points at close separation are sampled more extensively than points at long separation. A preferred embodiment is to use an alternating sequence of global and local refinement cycles, similar to the one described above. In this embodiment, a phase of global refinement is initially carried out. At the end of this phase, the resulting non-linear map is partitioned into a regular grid, and the points (objects) in each cell are subjected to a phase of local refinement (i.e. only points from within the same cell are compared and refined). Preferably, the number of sampling steps in each cell should be proportional to the number of points contained in that cell. This process is highly parallelizable. This local refinement phase is then followed by another global refinement phase, and the process is repeated for a prescribed number of cycles, or until the embedding error is minimized within a prescribed tolerance. Alternatively, the grid method may be replaced by another suitable method for identifying proximal points, such as a k-d tree, for example.

7.3 INCREMENTAL REFINEMENT

The approach and techniques described herein may be used for incremental refinement of a map. That is, starting from an organized non-linear map of a set of objects or points (compounds), a new set of objects (compounds) may be added without modification of the original map. Strictly speaking, this is statistically acceptable if the new set of objects is significantly smaller than the original set. In a preferred embodiment, the new set of objects may be 'diffused' into the existing map, using a modification of the algorithm described above. In particular, EQ. 8 and 9 can be used to update only the new objects. In addition, the sampling procedure ensures that the selected pairs contain at least one object from the incoming set. That is, two objects are selected at random so that at least one of these objects belongs to the incoming set.

8. OPERATION OF THE PRESENT INVENTION

Figure 3:
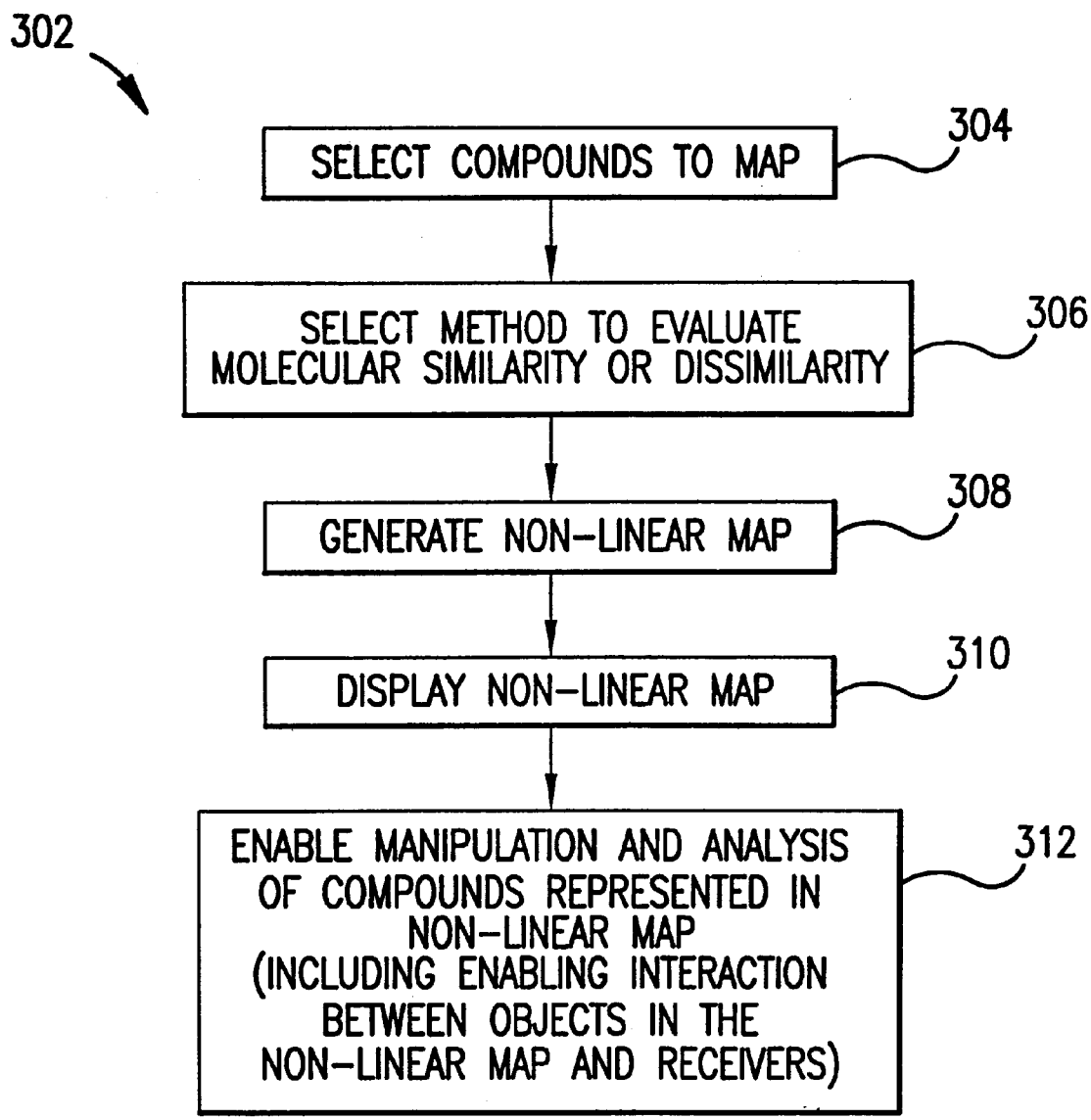
FIG. 3 is a flowchart representing the operation of the invention in visualizing and interactively processing non-linear maps according to an embodiment of the invention.

The operation of the present invention with regard to visualizing and interactively processing chemical compounds in a non-linear map shall now be described with reference to a flowchart 302 shown in FIG. 3. Unless otherwise specified, interaction with users described below is achieved by operation of the user interface modules 108 (FIG. 1).

In step 304, the user selects one or more compounds to map in a new non-linear map. The user may select compounds to map by retrieving a list of compounds from a file, by manually typing in a list of compounds, and/or by using a graphical user interface (GUI) such as the structure browser shown in FIG. 5 (described below). The invention envisions other means for enabling the user to specify compounds to display in a non-linear map. For example, the user can also select compounds from an already existing compound visualization non-linear map (in one embodiment. the user drags and drops the compounds from the old compound visualization non-linear map to the new compound visualization non-linear map—drag and drop operations according to the present invention are described below).

In step 306, the user selects a method to be used for evaluating the molecular similarity or dissimilarity between the compounds selected in step 304. In an embodiment, the similarity/dissimilarity between the compounds selected in step 304 is determined (in step 308) based on a prescribed set of evaluation properties. As described above, evaluation properties can be any properties related to the structure, function, or identity of the compounds selected in step 304. Evaluation properties include, but are not limited to, structural properties, functional properties, chemical properties, physical properties, biological properties, etc., of the compounds selected in step 304.

In an embodiment of the present invention, the selected evaluation properties may be scaled differently to reflect their relative importance in assessing the proximity (i.e., similarity or dissimilarity) between two compounds. Accordingly. also in step 306, the user selects a scale factor for each of the selected evaluation. Note that such selection of scale factors is optional. The user need not select a scale factor for each selected evaluation property. If the user does not select a scale factor for a given evaluation property, then that evaluation property is given a default scale factor, such as unity.

Alternatively in step 306, the user can elect to retrieve similarity/dissimilarity values pertaining, to the compounds selected in step 304 from a source, such as a database. These similarity/dissimilarity values in the database were previously generated. In another embodiment, the user in step 306 can elect to determine similarity/dissimilarity values using any well-known technique or procedure.

Figure 4:
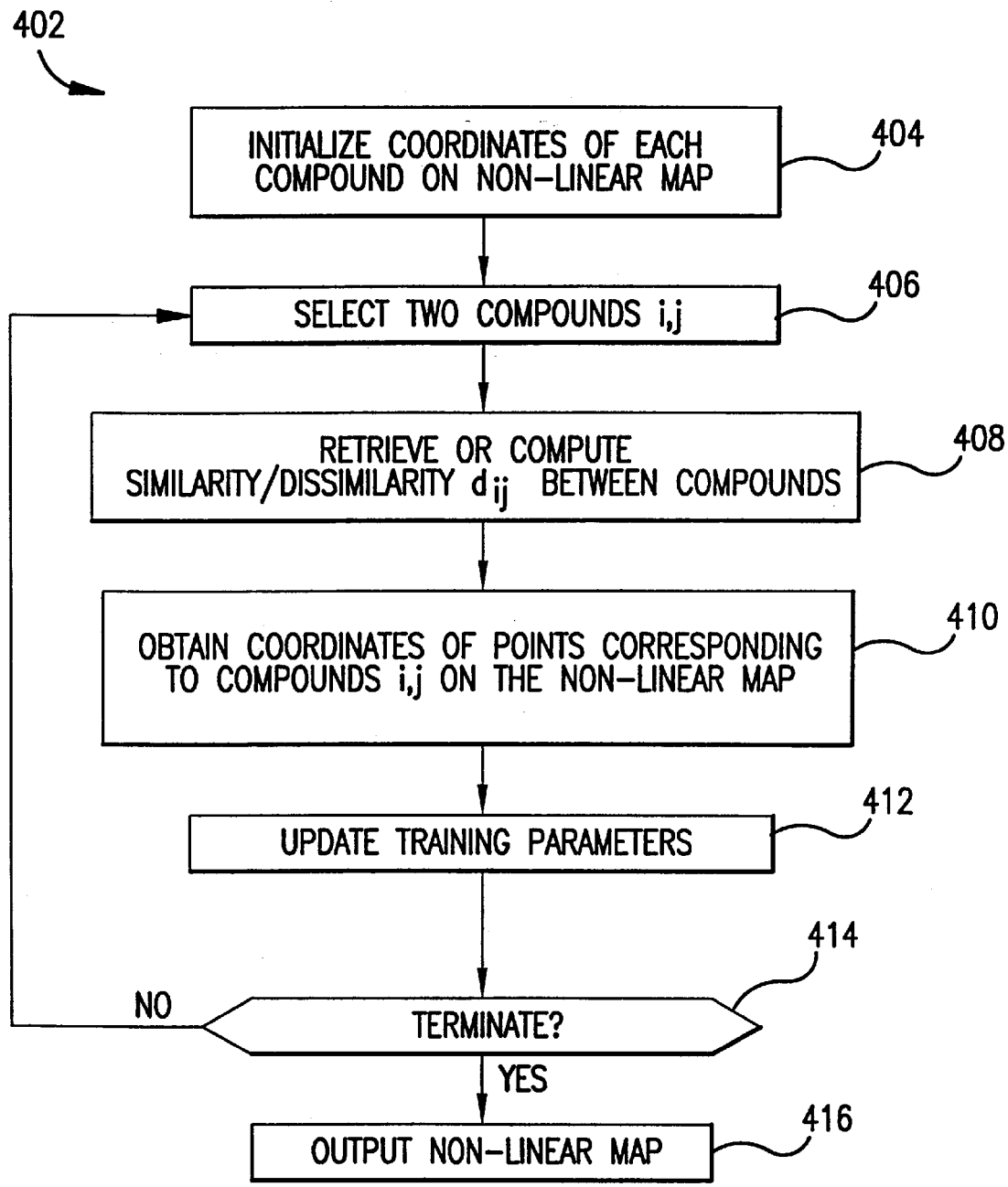
FIG. 4 is a flowchart representing the manner in which a non-linear map is generated according to an embodiment of the invention.

In step 308, the map generating module 106 generates a new non-linear map. This new non-linear map includes a point for each of the compounds selected in step 304. Also, in this new non-linear map, the distance between any two points is representative of their similarity/dissimilarity. The manner in which the map generating module 106 generates the new non-linear map shall now be further described with reference to a flowchart 402 in FIG. 4.

In step 404, coordinates on the new non-linear map of points corresponding to the compounds selected in step 304 are initialized.

In step 406, two of the compounds i, j selected in step 304 are selected for processing.

In step 408, similarity/dissimilarity $d_{ij}$ between compounds i, j is determined based on the method selected by the user in step 306.

In step 410, based on the similarity/dissimilarity $d_{ij}$ determined in step 408, coordinates of points corresponding to compounds i, j on the non-linear map are obtained.

In step 412. training/learning parameters are updated.

In step 414, a decision is made as to terminate or not terminate. If a decision is made to not terminate at this point, then control returns to step 406. Otherwise, step 416 is performed.

In step 416, the non-linear map is output (i.e., generation of the non-linear map is complete).

Details regarding the steps of flowchart 402 are discussed above.

Figure 6:
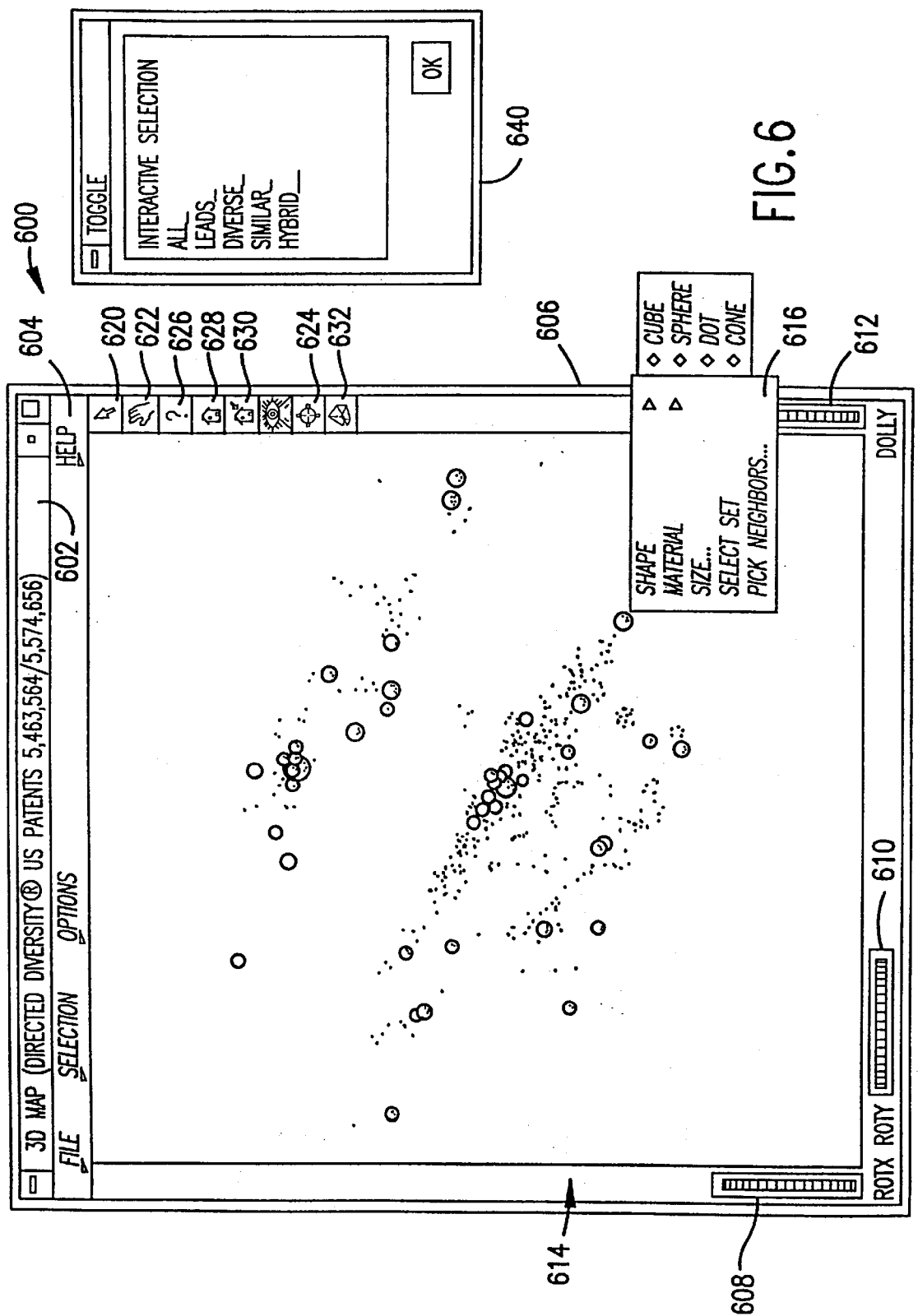
FIG. 6 illustrates a compound visualization non-linear map window according to an embodiment of the invention.
Figure 7:
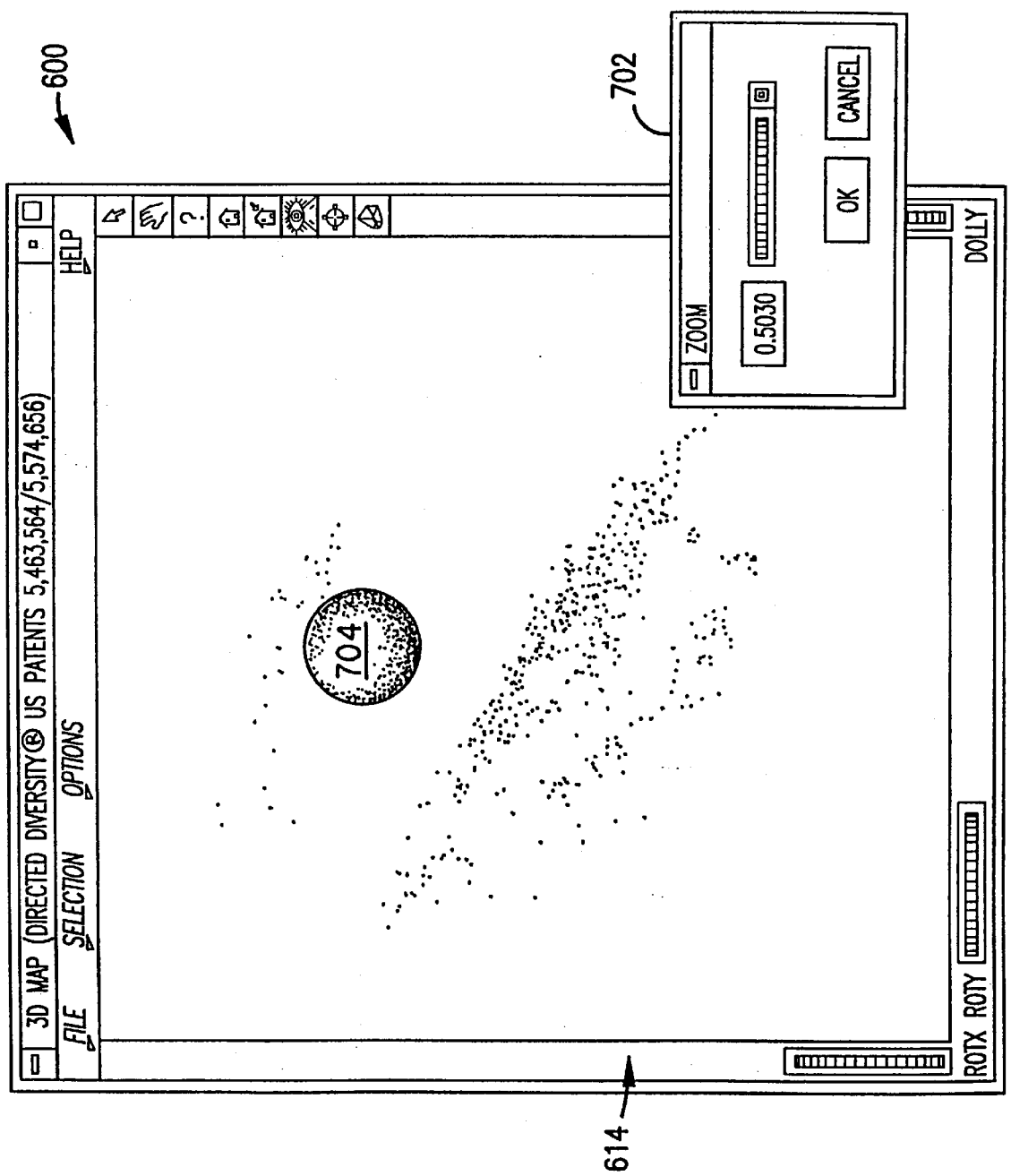
FIG. 7 is used to describe a zoom function of the present invention.

Referring again to FIG. 3, in step 312 the map viewer 112 displays the new non-linear map on an output device 116 (such as a computer graphics monitor). Examples of non-linear maps being displayed by the map viewer 112 are shown in FIGS. 6 and 7 (described below).

In step 314, the user interface modules 108 enable operators to interactively analyze and process the compounds represented in the displayed non-linear map. These user interface functions of the present invention are described below.

The present invention enables users to modify existing Compound visualization non-linear maps (as used herein, the term "compound visualization non-linear map" refers to a rendered non-linear map). For example, users can add additional compounds to the map, remove compounds from the map, highlight compounds on the map, etc. In such cases, pertinent functional steps of flowchart 302 are repeated. For example, steps 304 (selecting compounds to map), 310 (generating the non-linear map), and 312 (displaying the map) are repeated when the user opts to add new compounds to an existing map. However, according to an embodiment of the invention, the map is incrementally refined and displayed in steps 310 and 312 when adding compounds to an existing compound visualization non-linear map (this incremental refinement is described above).

9. USER INTERFACE OF THE PRESENT INVENTION

The user interface features of the present invention are described in this section. Various user interface modules and features are described below. Also, various functional/control threads (in the present context, a functional/control thread is a series of actions performed under the control of a user) employing these user interface modules and features are described below. It will be appreciated by persons skilled in the relevant art(s) that the user interface of the present invention is very flexible, varied, and diverse. An operator can employ the user interface of the present invention to perform a wide range of activities with respect to visualizing and interactively analyzing chemical compounds. Accordingly, it should be understood that the functional/control threads described herein are provided for illustrative purposes only. The invention is not limited to these functional/control threads.

Preferably, the invention provides the following capabilities, features. and functions: displaying 2D and/or 3D chemical structures and/or chemical names; displaying compound collections and/or libraries: displaying components of structures (i.e. building blocks) of combinatorial libraries; visualization of compound collections and/or libraries as 2D and/or 3D maps of colored objects.

Also, the present invention allows the following: (1) browsing compound collections and/or libraries; (2) selection of individual compounds, collections of compounds and/or libraries of compounds; (3) selection of compounds generated in a combinatorial fashion via selection of their respective building blocks; (4) mapping, visualization, and/or linking of compounds onto and/or from 2D and/or 3D maps; (5) manipulation of the 2D and/or 3D maps such as rotation, resizing, translation, etc.; (6) manipulation of objects on the 2D and/or 3D maps such as changing the appearance of objects (visibility, size, shape, color, etc.), changing position of objects on the map, and/or changing relationships between objects on the map; (7) interactive exploring of the 2D and/or 3D maps such as querying chemical structure, querying distance, selection of individual objects and/or areas of a map, etc.

Additional user interface features, functions, and capabilities of the present invention will be apparent to persons skilled in the relevant art(s) based oil the discussion contained herein.

As shown in FIG. 1 the invention includes a structure browser 110 and a map viewer 112. At any given time, each of these can have multiple instances depending on the program use.

9.1 STRUCTURE BROWSER

Figure 5:
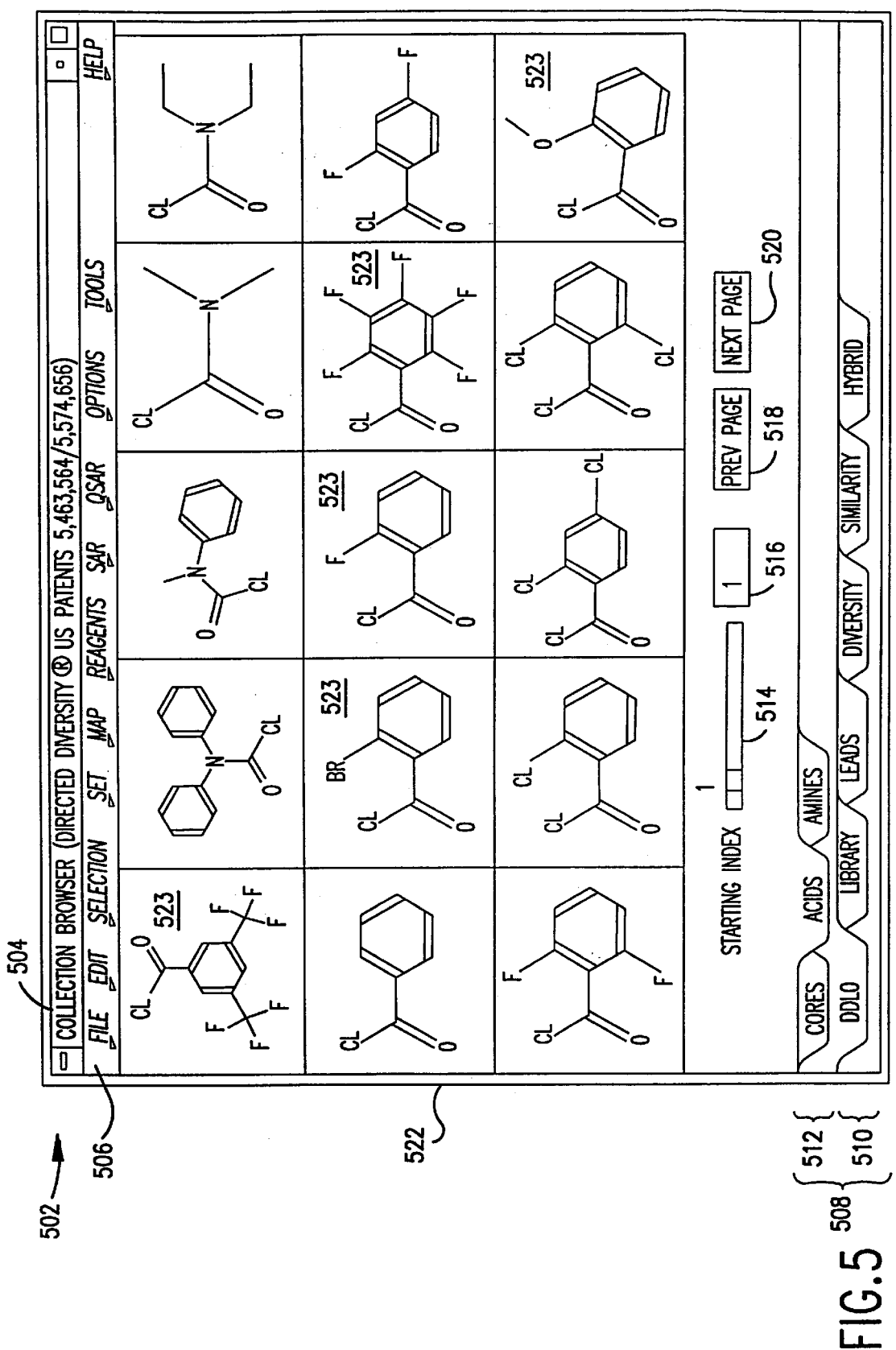
FIG. 5 illustrates a structure browser window according to an embodiment of the invention.

FIG. 5 illustrates a structure browser window 502 generated by the structure browser 110. The structure browser window 502 includes a frame 504, a menu pane 506, and a group of labeled tabbed pages 508. Each tabbed page holds a molecular spreadsheet or a group of labeled tabbed pages.

Each tab is associated with a compound collection (tabs 510) or a library. Such as a combinatorial library (tabs 512). Selecting a collection tab 510 brings up a table of corresponding chemical structures. Selecting a library tab 512 brings up a group of tabbed pages corresponding to the sets of building blocks used to generate the library. each of the library's tabbed pages works the same way as a compound collection tabbed page. In the example shown in FIG. 5, the tab 510 called "DDL0" is selected. DDL0 has three building block tabs 512. called "Cores." "Acids," and "Amines." The "Acids" collection tab is currently selected, so that a table 522 of the structures of the compounds in the "Acids" collection is shown.

The browser window 502 includes a table 522, a slider 514, an input field 516. and two buttons: "Prev Page" 518 and "Next Page" 520. The slider 514, the input field 516, and the buttons 518, 520 facilitate browsing the content of the Acids table 522. If we consider the content of the table 522 as a contiguous ordered list of chemical structures (compounds or building blocks), that shown in the browser window 502 can be considered as a window positioned over the list. At any given moment this window displays part of the list depending on its position and the displayed part is equal to the size of the window, i.e., the number of cells in the table. Initially that window displays the top of the list. Moving the slider 514 chances the position of the window over the list. Entering a value into the input field 516 specifies the position of the window, over the list. Pushing the "Next Page" button 520 moves the window one window size down the list, pushing the "Prev Page" button 518 moves the window one window size up the list.

The user can select compounds shown in the table 522 for various actions. For example, compounds can be selected using the browser window 502 as input for the generation of a new compound visualization non-linear map, or as input for adding compounds to an existing compound visualization non-linear map. Clicking with a left mouse button over a table cell selects or deselects the corresponding compound structure (toggling). Toggling on/off also changes the color of the cell, to indicate which cells have been selected. Selected structures are displayed on a first background color, and non-selected structures are displayed on a second background color. In the example of FIG. 5, certain cells 523 in table 522 have been selected.

Figure 8:
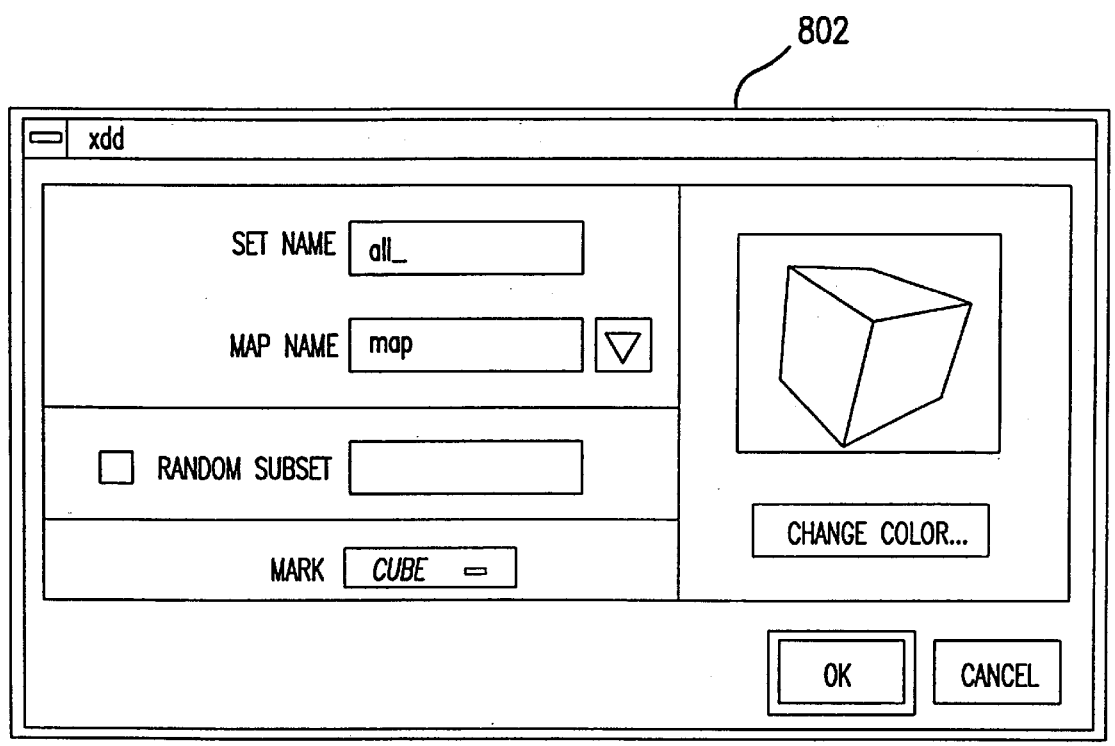
FIG. 8 illustrates a dialog used to adjust properties of a set containing one or more compounds.
Figure 9:
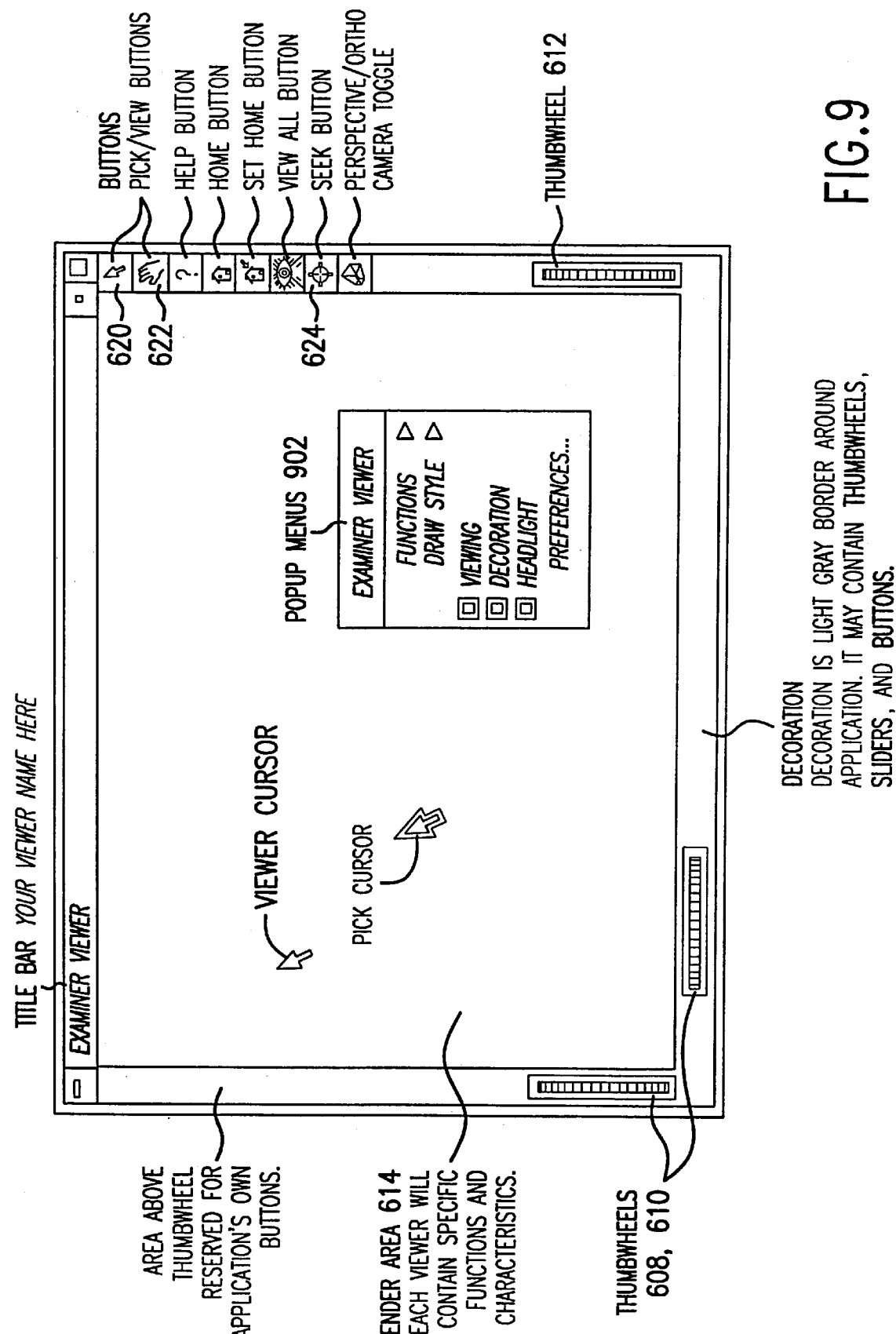
FIGS. 9 and 10 are used to describe the compound visualization non-linear map window according to an embodiment of the invention.
Figure 10:
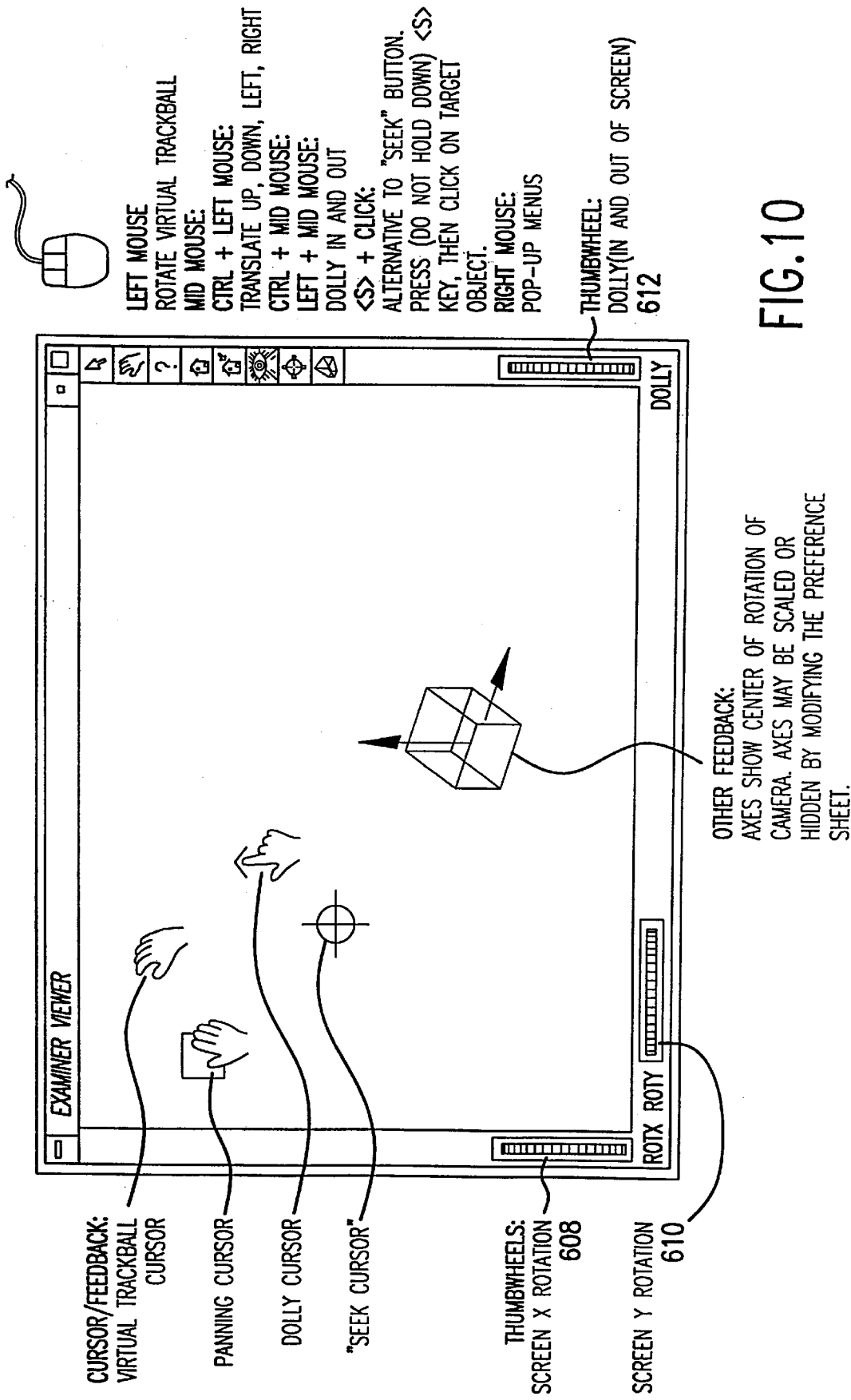
Figure 11:
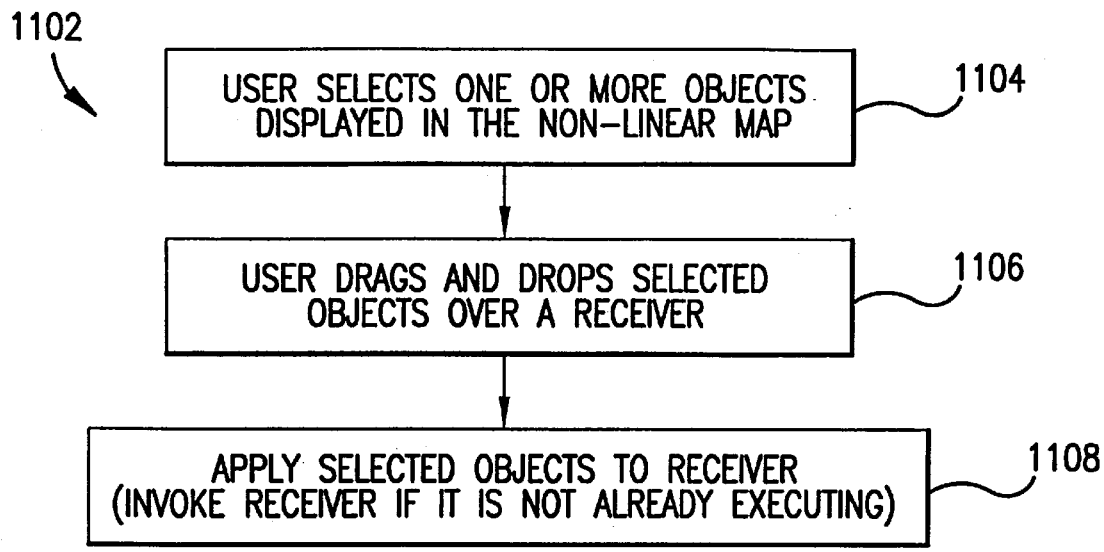
FIG. 11 is a flowchart illustrating the operation of the invention where a compound visualization non-linear map window is used as a source in an interactive operation.
Figure 12:
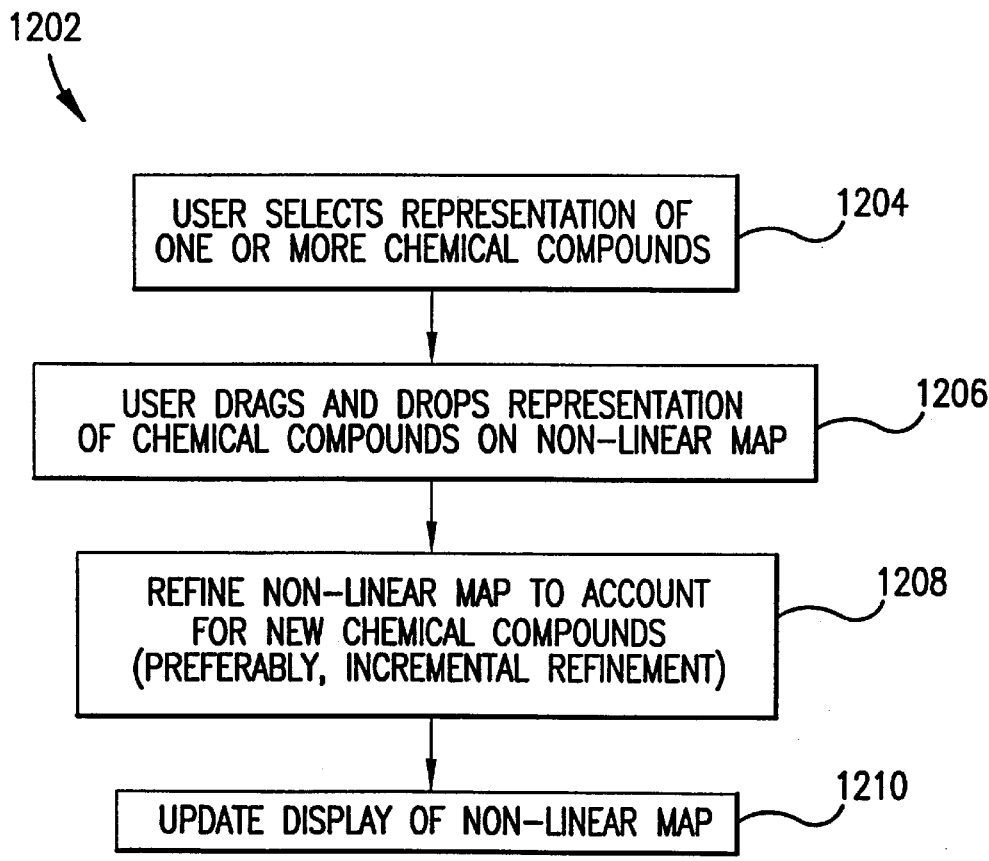
FIG. 12 is a flowchart illustrating the operation of the invention where a compound visualization non-linear map window is used as a target in an interactive operation.

The menu pane 506 contains menus: File, Edit, Selection, Map, and/or other menus. The File menu facilitates file open/save, print, and exit operations. Edit menu contains commands for editing content of the table 522. The Selection menu provides options to select/deselect (clear) a current compound collection, a collection of building blocks of a combinatorial library, and/or all compounds. The Map menu includes commands for creating a map viewer and for displaying a selection of compounds in that map viewer. The latter option brings up a dialog window (FIG. 8), which allows the user to specify shape, color, and/or size of the selected objects, which will be used to represent the selected compounds on the map.

9.2 MAP VIEWER

A map viewer window 600 generated by the map viewer 112 is shown in FIG. 6. (also see FIGS. 6–10 and 13). A compound visualization non-linear map is displayed in a render area 614 of the map view window 600.

In a preferred embodiment, the map viewer 112 is based on Open Inventor, a C++ library of objects and methods for interactive 3D graphics, publicly available from Silicon Graphics Inc. Open Inventor relies on OpenGL, for fast and flexible rendering of 3D objects. Alternatively, the map viewer 112 can be based on a publicly available VRML viewer. Alternatively, any other software and/or hardware product allowing rendering of 3D objects/scenes can be used.

In a preferred embodiment, 3D compound visualization maps of chemical compounds are implemented as Open Inventor 3D scene databases. Each map is build as an ordered collection of nodes referred to as a scene graph. Each scene graph includes, but is not limited to, nodes representing cameras (points of view), light sources, 3D shapes, objects surface materials, and geometric transformations. Each chemical compound displayed on a map is associated with a 3D shape node, a material node and a geometric transformation node.

Geometric transformation node reflects compound coordinates in the map. 3D shape node and material node determine shape, size and color of the visual object associated with the compound. Combinations of a particular shape, size and color are used to display compounds grouped by a certain criteria, thus allowing easy visual differentiation of different groups/sets of compounds. 3D shapes of the visual objects in the map include, but not limited to, point, cube, sphere, and cone. Color of a visual object in the map can be set to any combination of three basic colors: red, green and blue. Besides the color, material node can specify transparency and shininess of a visual object's surface.

In an embodiment, an object's display properties (color, intensity of color, transparent, degree of transparency, shininess, degree of shininess, etc.) can represent physical, chemical, biological, and/or other properties of the corresponding compound, such as the cost of the compound, difficulty of synthesizing the compound, whether the compound is available in a compound repository, etc. For example, the larger the molecular weight of an object, the larger tile size of the corresponding object in the display map.

Each object or point displayed in the compound visualization non-linear map represents a chemical compound. Objects in the compound visualization non-linear, map can be grouped into sets.

By default, every time a set of compounds is mapped into a compound visualization non-linear map, a new set of graphical objects is created and added to the compound visualization non-linear map. All objects in a particular set can share the same attributes: shape, color, and size, thus providing an easy visual identification of the objects belonging, to the same set or to different sets.

A compound can be a member of several sets. In an embodiment, for a given compound, a different object is displayed in the compound visualization non-linear, map for each get of which the compound is a member. In this case the objects in the compound visualization non-linear map that represent the compound as a member of each of the sets may overlap and only the biggest object may be visible. In this case, a toggle sets feature (described below) may be used to reveal multiple set membership.

The map viewer window 600 includes a frame 602, a menu pane 604, and a viewer module preferably implemented as an Open Inventor component (examiner viewer). The viewer module incorporates the following elements: (1) a render area 614 in which the compound visualization non-linear map is being displayed; (2) combinations of thumbwheels 608, 610, 612, sliders, and/or viewer functions icons/buttons 620, 622, 624, 626, 628, 630, 632; and (3) pop-up menus and dialogs 616, 702, 902 which provide access to all viewers functions, features and/or properties.

The thumbwheels 608, 610 rotate the compound visualization non-linear map around a reference point of interest. Thumbwheel 610 rotates in the y direction, and thumbwheel 608 rotates in the x direction. The origin of rotation (i.e., the camera position) is by default the geometric center of the compound visualization map 614 (render area), but can be placed anywhere in the compound visualization non-linear map. The compound visualization non-linear map can also be panned in the screen plane, as well as dollied in and out (forward/backward movement) via thumbwheel 612.

The map view window 600 has several different modes or states, e.g. view, pick, panning, dolly, seek, and/or other. Each mode defines a different mouse cursor and how mouse events are interpreted.

In the view mode, mouse motions are translated into rotations of the virtual trackball and corresponding rotations of the compound visualization non-linear map. The view mode is the default mode.

In the panning mode, the compound visualization non-linear map is translated in the screen plane following the mouse movements.

In the dolly mode, a scene is moved in and out of screen according to the vertical motions of the mouse.

Seek mode allows the user to change the point of rotation (reference point) of a scene by attaching it to an object displayed in the compound visualization non-linear map.

Pick mode is used for picking (querying) objects displayed in the compound visualization non-linear map. Picking an object in a 3D scene is achieved by projecting a conical ray from the camera through a point (defined by positioning and clicking the mouse) on the near plane of the view volume. The first object in the scene intersecting with the ray cone is picked. As a response to a pick event (an object being picked by pressing the left mouse button over the object), a small window displaying the corresponding compound pops up while the left mouse button is pressed (see, for example, window 1302 in FIG. 13). The window will automatically disappear when the button is released. In order to keep the window on the screen, it is necessary to hold the shift key while releasing the mouse button.

Switching between the above-described modes can be achieved by selecting a mode from a pop-up menu, by clicking on a shortcut icon/button, and/or by pressing and/or holding a combination of mouse buttons and/or keys on a keyboard. In a preferred embodiment, selecting a pointed arrow icon/button 620 switches to the pick mode. Selecting a hand icon/button 622 switches to the view mode, selecting a target icon/button 624 switches to the seek mode. Pressing and holding the middle mouse button switches to the panning mode. Pressing and holding the left and middle mouse buttons simultaneously switches to the dolly mode.

Certain actions can be executed also via thumbwheels and/or sliders, e.g. turning the dolly thumbwheel 612 moves the scene in and out of the screen. Also, turning the X and/or Y rotation thumbwheels 608, 610 rotate the scene accordingly around the point of rotation.

In a preferred embodiment, the right mouse button is reserved for the pop-up menus 616, 902. Pressing the right mouse button anywhere over an empty rendering area brings up the viewer pop-up menu 902. Pressing the right mouse button over an object brings up the object pop-up menu 616.

The viewer pop-up menu 902 allows the user to select the mode (such modes are described above), change viewer properties (set up preferences, e.g. background color), toggle on/off sets of objects, and/or access any other viewer features.

The object pop-up menu 616 allows the user to change an object's shape, color (material), and/or size, select the corresponding set of compounds, and/or define a neighborhood 3D area around the object (zoom feature, described below). In a preferred embodiment, all changes made to an object automatically apply to all other objects from the same set. The object's shape can be changed to one of the predefined basic shapes (e.g. dot, cube, sphere, cone). The object's material (color) is changed via a color dialog. The object's size is changed via a resize dialog. Any set of objects can be visible (toggled on) or hidden (toggled off). A toggle sets command brings up a list of sets defined for the current map 640. Clicking on a set in the list (highlighting/clearing) toggles the set off and on.

Invoking the zoom feature (via the pick neighbors command on the object pop-up menu 616, for example) creates a sphere 704 in the render area 614 (FIG. 7). which is centered on the object. The radius of the sphere 704 can be adjusted via a resize dialog 702 to select a desired neighborhood area around the object. All objects (and corresponding compounds) encompassed by the sphere 704 are then selected, displayed in a different map, added to a new or existing set, dragged to a target (described below), and/or viewed in a structure browser window 502.

The map viewer 112 is capable of maintaining an interactive selection of objects/compounds. All selected objects are visualized in the same shape, color, and/or size. In other words, selecting an object chances its shape, color, and/or size (e.g. to a purple cone), deselecting an object changes its shape, color and/or size back to the original attributes. Executing the select set command from the object pop-up menu 616 selects the whole set of obects this object belongs to. Alternatively, an individual object can be selected or deselcoted by clicking a middle mouse button over an object. The interactive selection of objects can be converted to a set of compounds and displayed in a structure browser window 502. The Current selection can be converted into a set of compounds by invoking the save selection command from a selection menu, and/or it can be cleared by executing the clear selection command drop in the selection menu.

9.3 INTERACTIVITY OF THE PRESENT INVENTION

As should be apparent from the above, the present invention enables users to interact with the objects/compounds displayed in a compound visualization non-linear map. This interactivity provided by the present invention shall be further illustrated below.

9.3.1 MAP VIEWER AS TARGET

According to the present invention a user can select a plurality of compounds from some source, and then add those compounds to a new or an existing compound visualization non-linear map being displayed in a map window 600. In this instance. the map window 600 (or equivalently in this context the map viewer 112) is acting as a target for an interactive user activity.

Figure 14:
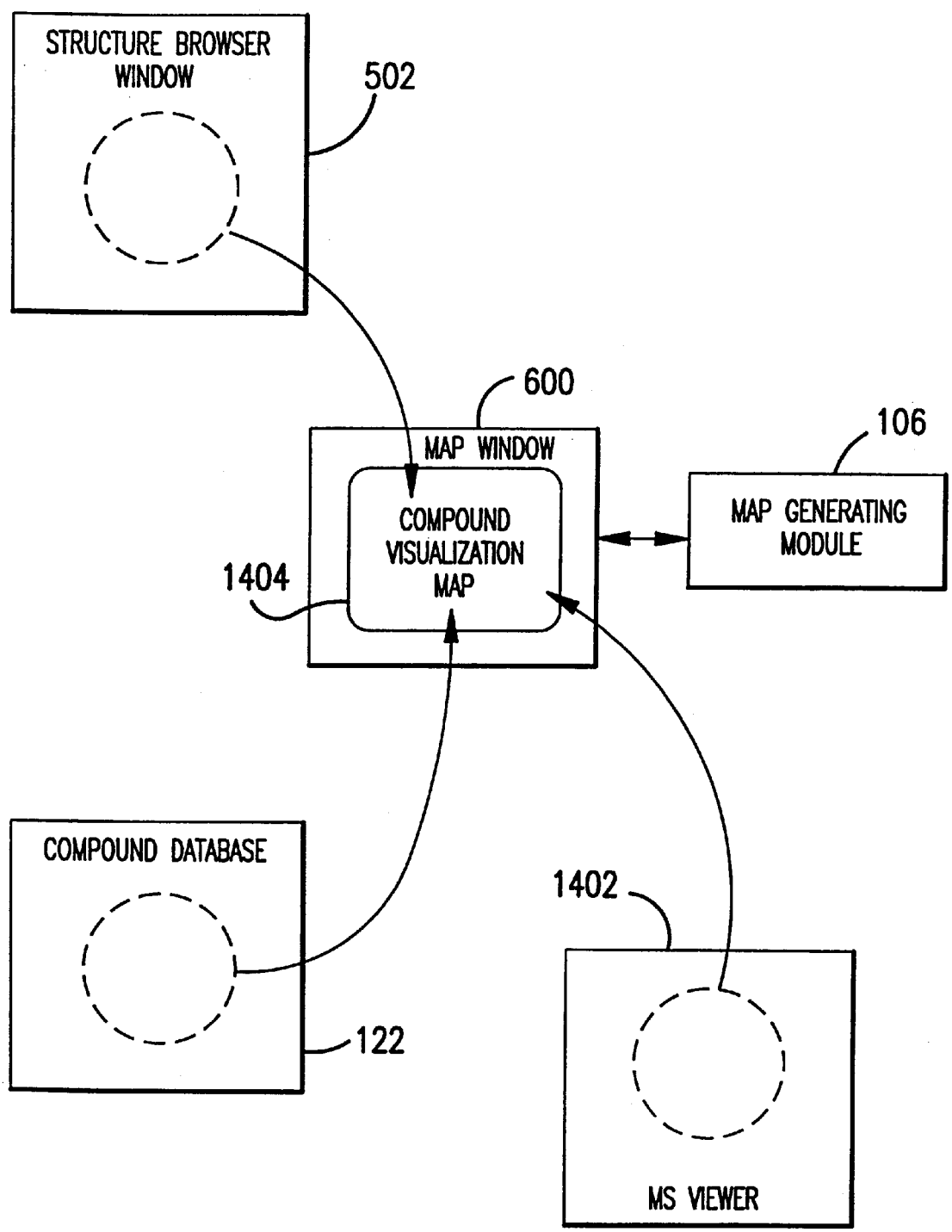
FIG. 14 conceptually illustrates an interactive operation where a compound visualization non-linear map window is used as a target.

This operation is conceptually shown in FIG. 14. A compound visualization non-linear map 1404 is being displayed in a map window 600. According to the present invention the user can select compounds from a structure browser window 502, and then add those selected compounds (through, for example, well known drag and drop operations) to the compound visualization non-linear map 1404. Similarly, the user can select compounds from a compound database 122, or frome a MS (mass spectrometry) viewer 1402, and then add those compounds to the compound visualization non-linear map 1404.

According to an embodiment of the invention, new compounds are added to an existing compound visualization non-linear map by incremental refinement of the compound visualization non-linear map. Such incremental refinement is described above.

9.3.2 MAP VIEWER AS SOURCE

According to the present invention, a user can select a plurality of compounds from a map window 600, and then have those compounds processed by a target. In this instance, the map window 600 (or, equivalently in this context. the map viewer 112) is acting as a source for an interactive user activity.

Figure 13:
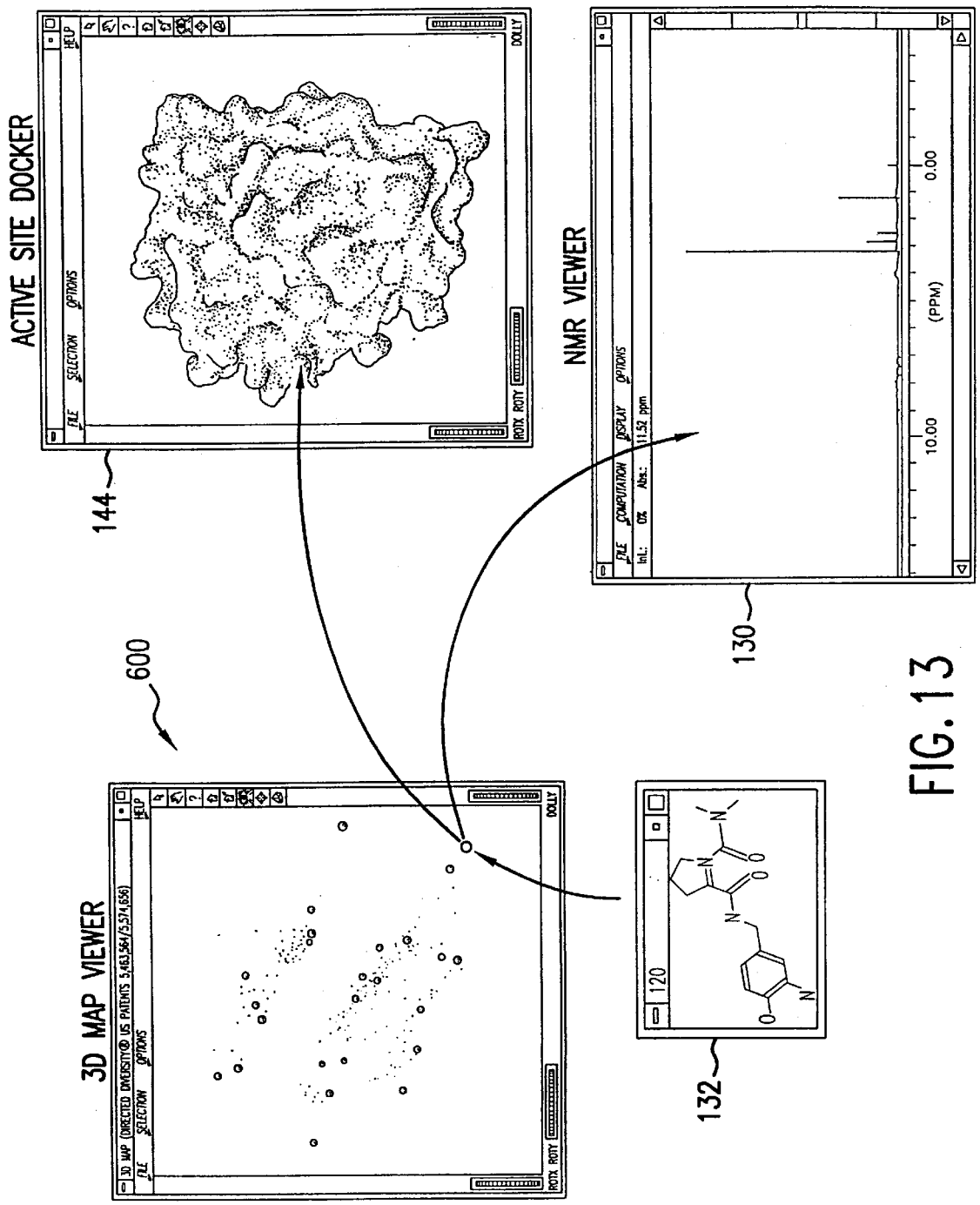
FIG. 13 conceptually illustrates an interactive operation where a compound visualization nonlinear map window is used as a source.

This operation is conceptually shown in FIG. 13. A user selects one or more compounds from the compound visualization non-linear map being displayed in the map window 600, and then drags and drops the selected compounds to a target. The described action is interpreted as a submission of the corresponding chemical structure(s) to the receiving target for processing. The receiving object can be anything that can handle a chemical structure: another map viewer 112, a structure viewer 110, a (molecular) spreadsheet 136, a database 120, an experiment planner 140, an active site docker 144, an NMR widget 130, an MS widget 134, a QSAR model 138, a property prediction program 142, or any other suitable process. For example, dragging and dropping a compound onto an NMR widget would display this compound's NMR spectrum, either an experimental or a predicted one.

The experiment planner is described in pending U.S. patent application titled "SYSTEM, METHOD AND COMPUTER PROGRAM PRODUCT FOR IDENTIFYING CHEMICAL COMPOUNDS HAVING DESIRED PROPERTIES," Atty. Docket No. 1503.0200001, herein incorporated by reference in its entirety.

The drag and drop concept described above provides a powerful enhancement of a 3D mapping and visualization of compound collections and libraries. Any conceivable information about a set of chemical compounds can thus be easily accessed from the compound visualization non-linear map. For example, a map of compounds capable of binding to an active site of a given enzyme or receptor would benefit from the possibility to visualize how compounds from the different areas of the map bind to that enzyme or receptor.

9.4 MULTIPLE MAPS

According to the present invention, it is possible to create multiple visual maps for any given set of collections and/or libraries of chemical compounds. Multiple visual maps can be based on the same and/or different non-linear maps. Visual maps based on the same non-linear map can display different subsets of compounds and/or present different views of the same set of compounds (e.g. one visual map can display an XY plane view and another visual map can display an orthogonal, YZ plane view). Visual maps based on different non-linear maps can visualize the same set of compounds on different projections, for example, maps derived from different similarity relations between these compounds.

If a compound is mapped on multiple visual maps, the visual objects representing the compound on the different maps can be crosslinked. Crosslinking means that any modifications made to a visual object in one of the visual maps will be automatically reflected into the other visual maps. For example, if an object is selected on one of the visual maps, it will be displayed as selected on the other visual maps as well. In fact, all objects on all maps can be crosslinked provided that they represent the same chemical compounds. Multiple visual maps can be also crosslinked in a way that mapping any additional compounds onto one of the visual maps will automatically map the same compounds onto the crosslinked maps.

10. EXAMPLES

The present invention is useful for visualizing and interactively processing any chemical entities including but not limited to small molecules. polymers, peptides, proteins, etc. It may also be used to display different similarity relationships between these compounds.

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention. These functional building blocks may be implemented by discrete components, application specific integrated circuits, processors executing appropriate software and the like or any combination thereof. It is well within the scope of one skilled in the relevant art(s) to develop the appropriate circuitry and/or software to implement these functional building blocks.

While various embodiments of the present invention have been described above, it should be understood that they have been presented by way of example only and not limitation. Thus, the breadth and scope of the present invention should not be limited by any of the above-described exemplary embodiments, but should be defined only in accordance with the following claims and their equivalents.

What is claimed is:

1. A method for representing similarity/dissimilarity between compounds, comprising the steps of:
   (1) generating an initial configuration of objects for display on a graphics device, the objects representing a plurality of compounds, each object having an initial set of coordinates;
   (2) selecting a subset of compounds from the plurality of compounds;
   (3) refining the coordinates of at least one object that represents a selected compound based on the coordinates of the at least one object, the coordinates of a second object, and a distance between the at least one and second objects so that a distance between the refined coordinates of the at least one object and the coordinates of the second object is more representative of the similarity/dissimilarity of the compounds;
   (4) repeating steps (2) and (3) for additional subsets of compounds; and
   (5) displaying at least some of the objects on the graphics device.

2. The method of claim 1, wherein step (1) compises the step of generating an initial configuration of objects at random.

3. The method of claim 1, wherein step (1) comprises the step of generating an initial configuration of objects using a semi-systematic procedure.

4. The method of claim 1, wherein step (1) comprises the step of generating an initial configuration of objects using a systematic procedure.

5. The method of claim 1, wherein step (1) comprises the step of generating an initial configuration of objects using values of a predefined set of molecular properties.

6. The method of claim 1, wherein step (1) comprises the steps of:
   (a) performing principal component analysis of data representing the plurality of compounds; and
   (b) generating an initial configuration of objects using the principal components that account for a significant portion of the variance in the data.

7. The method of claim 1, wherein step (2) comprises the step of selecting two compounds from the plurality of compounds.

8. The method of claim 7, wherein step (2) comprises the step of selecting two compounds with a probability of selection that is proportional to the separation distance of the objects so that objects located closer to each other are selected more frequently than objects located farther from each other.

9. The method of claim 7, wherein step (2) comprises the step of selecting two compounds with a probability that is proportional to the identity of the compounds so that certain predefined compounds are sampled more frequently than other compounds.

10. The method of claim 7, wherein step (2) comprises the step of selecting the subset of compounds based on one or more densities of their objects.

11. The method of claim 10, wherein step (2) further comprises the step of selecting compounds in higher density areas more often than objects in lower density areas.

12. The method of claim 10, wherein step (2) further comprises the step of selecting two compounds with a probability of selection that is proportional to the local density of the objects so that objects in low-density areas are selected with a lower probability than objects in high-density areas.

13. The method of claim 10, wherein step (2) further comprises the step of selecting two compounds with a probability of selection that is proportional to the local density of the objects so that objects in low-density areas are selected with a higher probability than objects in high-density areas.

14. The method of claim 7, wherein step (2) comprises the step of selecting two compounds with a probability of selection that is proportional to the separation distance of the objects so that objects located closer to each other are sampled less frequently than objects located farther from each other.

15. The method of claim 1, wherein step (2) comprises the step of selecting three compounds from the plurality of compounds.

16. The method of claim 1, wherein step (2) comprises the step of selecting the subset of compounds from the plurality of compounds at random.

17. The method of claim 1, wherein step (2) comprises the step of selecting the subset of compounds from the plurality of compounds using a semi-systematic procedure.

18. The method of claim 1, wherein step (2) comprises the step of selecting the subset of compounds from the plurality of compounds using a systematic procedure.

19. The method of claim 1, wherein step (3) comprises the step of:
   (a) refining the coordinates of at least one object based on molecular properties of the compounds selected in step (2) and a predetermined method for evaluating molecular similarity/dissimilarity.

20. The method of claim 19, wherein step (3)(a) comprises the step of refining the coordinates of at least one object based on the molecular shapes of the compounds selected in step (2).

21. The method of claim 19, wherein step (3)(a) comprises the step of refining the coordinates of at least one object based on electronic fields of the compounds selected in step (2).

22. The method of claim 19, wherein step (3)(a) comprises the step of refining the coordinates of at least one object based on steric fields of the compounds selected in step (2).

23. The method of claim 19, wherein step (3)(a) comprises the step of refining the coordinates of at least one object based on a user defined similarity/dissimilarity method.

24. The method of claim 19, wherein step (3)(a) comprises the step of refining the coordinates of at least one object based a plurality of molecular properties modified by weighting factors.

25. The method of claim 19, wherein step (3)(a) compises the step of refining the coordinates of at least one object based a plurality of molecular properties that are represented by a binary number.

26. The method of claim 1, wherein step (3) comprises the step of refining the coordinates of at least one object based on a user's input regarding the similarity/dissimilarity of the compounds selected in step (2).

27. The method of claim 1, wherein step (4) comprises the step of repeating steps (2) and (3) a predefined number of times.

28. The method of claim 1, wherein step (4) comprises the steps of:
 (a) selecting an error criterion; and
 (b) repeating steps (2) and (3) until the error criterion reaches a predefined threshold.

29. The method of claim 1, wherein step (4) comprises the step of repeating steps (2) and (3) until a predefined time limit has been exceeded.

30. The method of claim 1, further comprising the step of:
 (6) receiving input from a user regarding which compounds to represents by objects.

31. The method of claim 30, further comprising the step of:
 (7) receiving input from a user regarding which method to use for evaluating the similarity/dissimilarity of compounds.

32. The method of claim 31, further comprising the step of:
 (8) receiving input from a user regarding a dimensionality to be used in creating a non-linear map.

33. The method of claim 32, further comprising the step of:
 (9) generating the non-linear map based on the input received in steps (6) through (8).

34. The method of claim 33, further comprising the step of:
 (10) receiving input from a user about a compound selected for further evaluation.

35. A method for representing similarity/dissimilarity between compounds, comprising the steps of:
 (1) generating an initial configuration of objects for output, the objects representing a plurality of compounds, each object having an initial set of coordinates;
 (2) selecting a subset of compounds from the plurality of compounds;
 (3) refining the coordinates of at least one object that represents a selected compound based on the coordinates of the at least one object, the coordinates of a second object, and a distance between the at least one and second objects so that a distance between the refined coordinates of the at least one object and the coordinates of the second object is more representative of the similarity/dissimilarity of the compounds;
 (4) repeating steps (2) and (3) for additional subsets of compounds; and
 (5) outputting the coordinates of at least some of the objects.

36. The method of claim 35, wherein step (5) comprises the step of outputting the coordinates to a graphics device.

37. The method of claim 35, wherein step (5) comprises the step of outputting the coordinates to a data storage device.

38. The method of claim 35, wherein step (5) comprises the step of outputting the coordinates to a data table.

39. The method of claim 35, further comprising the step of:
 (6) generating structure-activity conelations for compounds using the coordinates output in step (5).

40. The method of claim 35, further comprising the step of:
 (6) generating structure-property correlations for compounds using the coordinates output in step (5).

41. A system for representing similarity/dissimilarity between compounds, comprising:
 a module that generates an initial configuration of objects for display on a graphics device, the objects representing a plurality of compounds, each object having an initial set of coordinates;
 a module that selects a subset of compounds from the plurality of compounds;
 a module that refines the coordinates of at least one object that represents a selected compound based on the coordinates of the at least one object, the coordinates of a second object, and a distance between the at least one and second objects so that a distance between the refined coordinates of the at least one object and the coordinates of the second object is more representative of the similarity/dissimilarity of the compounds; and
 a module that displays at least some of the objects on the graphics device.

42. A computer program product for representing similarity/dissimilarity between compounds, comprising a computer useable medium having computer program logic stored therein, wherein the computer program logic comprises:
 means for enabling a computer to generate an initial configuration of objects for display on a graphics device, the objects representing a plurality of compounds, each object having an initial set of coordinates;
 means for enabling a computer to select a subset of compounds from the plurality of compounds;
 means for enabling a computer to refine the coordinates of at least one object that represents a selected compound based on the coordinates of the at least one object, the coordinates of a second object, and a distance between the at least one and second objects so that a distance between the refined coordinates of the at least one object and the coordinates of the second object is more representative of the similarity/dissimilarity of the compounds; and
 means for enabling a computer to display at least some of the objects on the graphics device.

* * * * *